United States Patent
Jarjour et al.

(10) Patent No.: US 12,291,560 B2
(45) Date of Patent: May 6, 2025

(54) DIMERIZING AGENT REGULATED IMMUNORECEPTOR COMPLEXES

(71) Applicant: Regeneron Pharmaceuticals, Inc., Tarrytown, NY (US)

(72) Inventors: Jordan Jarjour, Seattle, WA (US); Wai-Hang Leung, Seattle, WA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 956 days.

(21) Appl. No.: 17/312,116

(22) PCT Filed: Dec. 13, 2019

(86) PCT No.: PCT/US2019/066241
§ 371 (c)(1),
(2) Date: Jun. 9, 2021

(87) PCT Pub. No.: WO2020/123947
PCT Pub. Date: Jun. 18, 2020

(65) Prior Publication Data
US 2022/0025014 A1    Jan. 27, 2022

Related U.S. Application Data

(60) Provisional application No. 62/835,662, filed on Apr. 18, 2019, provisional application No. 62/779,953, filed on Dec. 14, 2018.

(51) Int. Cl.
| | |
|---|---|
| C07K 16/28 | (2006.01) |
| A61K 35/17 | (2015.01) |
| A61K 39/00 | (2006.01) |
| A61P 35/02 | (2006.01) |
| C07K 14/705 | (2006.01) |
| C07K 14/73 | (2006.01) |
| C12N 15/86 | (2006.01) |
| A61K 38/00 | (2006.01) |

(52) U.S. Cl.
CPC .... *C07K 14/70517* (2013.01); *A61K 39/4611* (2023.05); *A61K 39/4631* (2023.05); *A61K 39/464411* (2023.05); *A61P 35/02* (2018.01); *C07K 14/70514* (2013.01); *C07K 14/70578* (2013.01); *C12N 15/86* (2013.01); *A61K 38/00* (2013.01); *C07K 2317/622* (2013.01); *C07K 2319/03* (2013.01); *C07K 2319/20* (2013.01); *C07K 2319/33* (2013.01); *C07K 2319/70* (2013.01); *C07K 2319/92* (2013.01)

(58) Field of Classification Search
CPC ........ C07K 14/70517; C07K 14/70514; C07K 14/70578; C07K 2319/03; C07K 2319/20; C07K 2319/33; C07K 2319/70; C07K 2319/92; A61P 35/02; C12N 15/86; A61K 38/00

See application file for complete search history.

(56) References Cited

U.S. PATENT DOCUMENTS

| | | |
|---|---|---|
| 4,751,180 A | 6/1988 | Cousens et al. |
| 4,935,233 A | 6/1990 | Bell et al. |
| 5,871,753 A | 2/1999 | Crabtree et al. |
| 5,910,573 A | 6/1999 | Pluckthun et al. |
| 6,291,158 B1 | 9/2001 | Winter et al. |
| 6,291,161 B1 | 9/2001 | Lerner et al. |
| 6,423,498 B1 | 7/2002 | Markland et al. |
| 6,649,595 B2 | 11/2003 | Clackson et al. |
| 6,692,736 B2 | 2/2004 | Yu et al. |
| 6,972,193 B1 | 12/2005 | Crabtree et al. |
| 9,587,020 B2 | 3/2017 | Wu et al. |
| 10,196,444 B2 | 2/2019 | Jarjour et al. |
| 10,287,354 B2 | 5/2019 | Brogdon et al. |
| 10,428,142 B2 | 10/2019 | Jarjour et al. |
| 10,457,731 B2 | 10/2019 | Jarjour et al. |
| 2003/0147869 A1 | 8/2003 | Riley et al. |
| 2007/0065431 A1 | 3/2007 | Coia et al. |
| 2011/0286980 A1 | 11/2011 | Brenner |
| 2012/0100160 A1 | 4/2012 | Lucas et al. |
| 2013/0287752 A1 | 10/2013 | Davila et al. |

(Continued)

FOREIGN PATENT DOCUMENTS

| | | |
|---|---|---|
| JP | 2002-503667 A | 2/2002 |
| JP | 2002-508971 A | 3/2002 |

(Continued)

OTHER PUBLICATIONS

Abate-Daga et al., CAR models: next-generation CAR modifications for enhanced T-cell function. Mol Ther Oncolytics. May 18, 2016;3:16014, 7 pages.
Alder et al., Antibody responses of variable lymphocyte receptors in the lamprey. Nat Immunol. Mar. 2008;9(3):319-27.
Banaszynski et al., Characterization of the FKBP•Rapamycin•FRB Ternary Complex. J Am Chem Soc. 2005;127(13):4715-4721.
Baral et al., Experimental therapy of African trypanosomiasis with a nanobody-conjugated human trypanolytic factor. Nat Med. May 2006;12(5):580-4.

(Continued)

*Primary Examiner* — Julie Ha
*Assistant Examiner* — Kristina M Hellman
(74) *Attorney, Agent, or Firm* — McCarter & English, LLP; Marcie B. Clarke; Dylan M. Blumenthal

(57) ABSTRACT

The present disclosure provides improved compositions for adoptive T cell therapies targeting CD33 for treating, preventing, or ameliorating at least one symptom of a cancer, infectious disease, autoimmune disease, inflammatory disease, and immunodeficiency, or condition associated therewith. The present disclosure also relates to adoptive T cell therapies targeting CD33 and another target antigen for treating, preventing, or ameliorating at least one symptom of a cancer, infectious disease, autoimmune disease, inflammatory disease, and immunodeficiency, or condition associated therewith.

10 Claims, 5 Drawing Sheets
Specification includes a Sequence Listing.

(56) References Cited

U.S. PATENT DOCUMENTS

| | | | |
|---|---|---|---|
| 2015/0266973 | A1 | 9/2015 | Jarjour et al. |
| 2016/0017302 | A1 | 1/2016 | Dotti et al. |
| 2016/0185862 | A1 | 6/2016 | Wu et al. |
| 2016/0311901 | A1* | 10/2016 | Jarjour .................. A61P 35/00 |
| 2020/0071399 | A1 | 3/2020 | Jarjour et al. |
| 2020/0071401 | A1 | 3/2020 | Jarjour et al. |
| 2022/0031750 | A1 | 2/2022 | Jarjour et al. |
| 2022/0324942 | A1 | 10/2022 | Jarjour et al. |

FOREIGN PATENT DOCUMENTS

| | | |
|---|---|---|
| WO | WO-1991/009058 A1 | 6/1991 |
| WO | WO-1999/036553 A2 | 7/1999 |
| WO | WO-1999/041258 A1 | 8/1999 |
| WO | WO-2003/057171 A2 | 7/2003 |
| WO | WO-2004/043344 A2 | 5/2004 |
| WO | WO-2006/072620 A1 | 7/2006 |
| WO | WO-2006/095164 A1 | 9/2006 |
| WO | WO-2007/098934 A1 | 9/2007 |
| WO | WO-2012/082841 A2 | 6/2012 |
| WO | WO-2014/127261 A1 | 8/2014 |
| WO | WO-2015/017214 A1 | 2/2015 |
| WO | WO-2015/150526 A2 | 10/2015 |
| WO | WO-2015/150771 A1 | 10/2015 |
| WO | WO-2016/014553 A1 | 1/2016 |
| WO | WO-2016/014576 A1 | 1/2016 |
| WO | WO-2017/180993 A1 | 10/2017 |
| WO | WO-2017/214333 A1 | 12/2017 |

OTHER PUBLICATIONS

Barthelemy et al., Comprehensive analysis of the factors contributing to the stability and solubility of autonomous human VH domains. J Biol Chem. Feb. 8, 2008;283(6):3639-3654.

Bayle et al., Rapamycin analogs with differential binding specificity permit orthogonal control of protein activity. Chem Biol. Jan. 2006;13(1):99-107.

Beavil et al., Alpha-helical coiled-coil stalks in the low-affinity receptor for IgE (Fc epsilon RII/CD23) and related C-type lectins. Proc Natl Acad Sci U S A. Jan. 15, 1992;89(2):753-7.

Belshaw et al., Controlling protein association and subcellular localization with a synthetic ligand that induces heterodimerization of proteins. Proc Natl Acad Sci U S A. May 14, 1996;93(10):4604-7.

Beste et al., Small antibody-like proteins with prescribed ligand specificities derived from the lipocalin fold. Proc Natl Acad Sci U S A. Mar. 2, 1999;96(5):1898-903.

Binz et al., Designing repeat proteins: well-expressed, soluble and stable proteins from combinatorial libraries of consensus ankyrin repeat proteins. J Mol Biol. Sep. 12, 2003;332(2):489-503.

Binz et al., Engineering novel binding proteins from nonimmunoglobulin domains. Nat Biotechnol. Oct. 2005;23(10):1257-68.

Bird et al., Single-chain antigen-binding proteins. Science. Oct. 21, 1988;242(4877):423-6.

Brentjens et al., CD19-targeted T cells rapidly induce molecular remissions in adults with chemotherapy-refractory acute lymphoblastic leukemia. Sci Transl Med. Mar. 20, 2013;5(177):177ra38.

Brentjens et al., Safety and persistence of adoptively transferred autologous CD19-targeted T cells in patients with relapsed or chemotherapy refractory B-cell leukemias. Blood. Nov. 3, 2011;118(18):4817-28.

Brown et al., A mammalian protein targeted by G1-arresting rapamycin-receptor complex. Nature. Jun. 30, 1994;369(6483):756-8.

Capon et al., Designing CD4 immunoadhesins for AIDS therapy. Nature. Feb. 9, 1989;337(6207):525-31.

Carpenito et al., Control of large, established tumor xenografts with genetically retargeted human T cells containing CD28 and CD137 domains. Proc Natl Acad Sci U S A. Mar. 3, 2009;106(9):3360-5.

Challita et al., Multiple modifications in cis elements of the long terminal repeat of retroviral vectors lead to increased expression and decreased DNA methylation in embryonic carcinoma cells. J Virol. Feb. 1995;69(2):748-55.

Chaudhary et al., A rapid method of cloning functional variable-region antibody genes in *Escherichia coli* as single-chain immunotoxins. Proc Natl Acad Sci U S A. Feb. 1990;87(3):1066-70.

Cooper et al., T-cell clones can be rendered specific for CD19: toward the selective augmentation of the graft-versus-B-lineage leukemia effect. Blood. Feb. 15, 2003;101(4):1637-44.

Cortez-Retamozo et al., Efficient cancer therapy with a nanobody-based conjugate. Cancer Res. Apr. 15, 2004;64(8):2853-7.

Craik et al., Plant cyclotides: A unique family of cyclic and knotted proteins that defines the cyclic cystine knot structural motif. J Mol Biol. Dec. 17, 1999;294(5):1327-36.

Curran et al., Chimeric antigen receptors for T cell immunotherapy: current understanding and future directions. J Gene Med. Jun. 2012;14(6):405-15.

De Felipe et al., Targeting of proteins derived from self-processing polyproteins containing multiple signal sequences. Traffic. Aug. 2004;5(8):616-26.

Desjarlais et al., Length-encoded multiplex binding site determination: application to zinc finger proteins. Proc Natl Acad Sci U S A. Nov. 8, 1994;91(23):11099-103.

Desjarlais et al., Use of a zinc-finger consensus sequence framework and specificity rules to design specific DNA binding proteins. Proc Natl Acad Sci U S A. Mar. 15, 1993;90(6):2256-60.

Donnelly et al., The 'cleavage' activities of foot-and-mouth disease virus 2A site-directed mutants and naturally occurring '2A-like' sequences. J Gen Virol. May 2001;82(Pt 5):1027-1041.

Dotti et al., Design and development of therapies using chimeric antigen receptor-expressing T cells. Immunol Rev. Jan. 2014;257(1):107-26.

Duke et al., Sequence and structural elements that contribute to efficient encephalomyocarditis virus RNA translation. J Virol. Mar. 1992;66(3):1602-9.

Duong et al., Enhancing the specificity of T-cell cultures for adoptive immunotherapy of cancer. Immunotherapy. Jan. 2011;3(1):33-48.

Fegan et al., Chemically controlled protein assembly: techniques and applications. Chem Rev. Jun. 9, 2010;110(6):3315-36.

Ghahroudi et al., Selection and identification of single domain antibody fragments from camel heavy-chain antibodies. FEBS Lett. Sep. 15, 1997;414(3):521-6.

Grunberg et al., Building blocks for protein interaction devices. Nucleic Acids Res. May 2010;38(8):2645-62.

Grupp et al., Chimeric antigen receptor-modified T cells for acute lymphoid leukemia. N Engl J Med. Apr. 18, 2013;368(16):1509-1518.

Haas et al., The Moloney murine leukemia virus repressor binding site represses expression in murine and human hematopoietic stem cells. J Virol. Sep. 2003;77(17):9439-50.

Hackel et al., Picomolar affinity fibronectin domains engineered utilizing loop length diversity, recursive mutagenesis, and loop shuffling. J Mol Biol. Sep. 19, 2008;381(5):1238-52.

Hamers-Casterman et al., Naturally occurring antibodies devoid of light chains. Nature. Jun. 3, 1993;363(6428):446-8.

Herrin et al., Structure and specificity of lamprey monoclonal antibodies. Proc Natl Acad Sci USA. Feb. 12, 2008;105(6):2040-5.

Hoet et al., Generation of high-affinity human antibodies by combining donor-derived and synthetic complementarity-determining-region diversity. Nat Biotechnol. Mar. 2005;23(3):344-8.

Hsu et al., Primary human T lymphocytes engineered with a codon-optimized IL-15 gene resist cytokine withdrawal-induced apoptosis and persist long-term in the absence of exogenous cytokine. J Immunol. Dec. 1, 2005;175(11):7226-34.

Hu et al., Minibody: A novel engineered anti-carcinoembryonic antigen antibody fragment (single-chain Fv-CH3) which exhibits rapid, high-level targeting of xenografts. Cancer Res. Jul. 1, 1996;56(13):3055-61.

Huang et al., Scorpion-toxin mimics of CD4 in complex with human immunodeficiency virus gp120 crystal structures, molecular mimicry, and neutralization breadth. Structure. May 2005;13(5):755-68.

Huez et al., Two independent internal ribosome entry sites are involved in translation initiation of vascular endothelial growth factor mRNA. Mol Cell Biol. Nov. 1998;18(11):6178-90.

(56) References Cited

OTHER PUBLICATIONS

Irion et al., Identification and targeting of the ROSA26 locus in human embryonic stem cells. Nat Biotechnol. Dec. 2007;25(12):1477-82.

Jackson et al., Internal initiation of translation in eukaryotes: the picornavirus paradigm and beyond. RNA. Dec. 1995;1(10):985-1000.

Jackson et al., The novel mechanism of initiation of picornavirus RNA translation. Trends Biochem Sci. Dec. 1990;15(12):477-83.

Janeway et al., Immunobiology: The Immune System in Health and Disease, 4th Edition. Current Biology Publications. pp. 148, 149 and 172, (1999).

Jespers et al., Aggregation-resistant domain antibodies selected on phage by heat denaturation. Nat Biotechnol. Sep. 2004;22(9):1161-5.

June et al., T-cell therapy at the threshold. Nat Biotechnol. Jul. 10, 2012;30(7):611-4.

Kalos et al., T cells with chimeric antigen receptors have potent antitumor effects and can establish memory in patients with advanced leukemia. Sci Transl Med. Aug. 10, 2011;3(95):95ra73.

Kay, Structure-function relationships in the FK506-binding protein (FKBP) family of peptidylprolyl cis-trans isomerases. Biochem J. Mar. 1, 1996;314(Pt 2)(Pt 2):361-85.

Kim et al., Hybrid restriction enzymes: zinc finger fusions to Fok I cleavage domain. Proc Natl Acad Sci U S A. Feb. 6, 1996;93(3):1156-60.

Klemm et al., Dimerization as a regulatory mechanism in signal transduction. Annu Rev Immunol. 1998;16:569-92.

Kochenderfer et al., B-cell depletion and remissions of malignancy along with cytokine-associated toxicity in a clinical trial of anti-CD19 chimeric-antigen-receptor-transduced T cells. Blood. Mar. 22, 2012;119(12):2709-20.

Kochenderfer et al., Treating B-cell cancer with T cells expressing anti-CD19 chimeric antigen receptors. Nat Rev Clin Oncol. May 2013;10(5):267-76.

Kowolik et al., D28 costimulation provided through a CD19-specific chimeric antigen receptor enhances in vivo persistence and antitumor efficacy of adoptively transferred T cells. Cancer Res. Nov. 15, 2006;66(22):10995-1004.

Lee et al., Design of a binding scaffold based on variable lymphocyte receptors of jawless vertebrates by module engineering. Proc Natl Acad Sci U S A. Feb. 28, 2012;109(9):3299-304.

Leung et al., Small Molecule-Regulated Antigen Recognition System for Inducible T Cell Targeting of CAncer Cells. Mol Ther. 2016;24:S110, Abstract No. 277.

Liu et al., Design of polydactyl zinc-finger proteins for unique addressing within complex genomes. Proc Natl Acad Sci U S A. May 27, 1997;94(11):5525-30.

Main et al., Design of stable alpha-helical arrays from an idealized TPR motif. Structure. May 2003;11(5):497-508.

Manzke et al., CD3X anti-nitrophenyl bispecific diabodies: universal immunotherapeutic tools for retargeting T cells to tumors. Int J Cancer. Aug. 27, 1999;82(5):700-8.

Maratea et al., Deletion and fusion analysis of the phage phi X174 lysis gene E. Gene. 1985;40(1):39-46.

Martin et al., Rational design of a CD4 mimic that inhibits HIV-1 entry and exposes cryptic neutralization epitopes. Nat Biotechnol. Jan. 2003;21(1):71-6.

Milone et al., Chimeric receptors containing CD137 signal transduction domains mediate enhanced survival of T cells and increased antileukemic efficacy in vivo. Mol Ther. Aug. 2009;17(8):1453-64.

Murphy et al., Genetic construction, expression, and melanoma-selective cytotoxicity of a diphtheria toxin-related alpha-melanocyte-stimulating hormone fusion protein. Proc Natl Acad Sci U S A. Nov. 1986;83(21):8258-62.

Nguyen et al., Heavy-chain antibodies in Camelidae; a case of evolutionary innovation. Immunogenetics. Apr. 2002;54(1):39-47.

Nguyen et al., The specific variable domain of camel heavy-chain antibodies is encoded in the germline. J Mol Biol. Jan. 23, 1998;275(3):413-8.

Nord et al., A combinatorial library of an alpha-helical bacterial receptor domain. Protein Eng. Jun. 1995;8(6):601-8.

Nord et al., Binding proteins selected from combinatorial libraries of an alpha-helical bacterial receptor domain. Nat Biotechnol. Aug. 1997;15(8):772-7.

Nord et al., Recombinant human factor VIII-specific affinity ligands selected from phage-displayed combinatorial libraries of protein A. Eur J Biochem. Aug. 2001;268(15):4269-77.

Parker et al., Antibody mimics based on human fibronectin type three domain engineered for thermostability and high-affinity binding to vascular endothelial growth factor receptor two. Protein Eng Des Sel. Sep. 2005;18(9):435-44.

Patel et al., Impact of chimeric immune receptor extracellular protein domains on T cell function. Gene Ther. Mar. 1999;6(3):412-9.

Pomerantz et al., Analysis of homeodomain function by structure-based design of a transcription factor. Proc Natl Acad Sci U S A. Oct. 10, 1995;92(21):9752-6.

Pomerantz et al., Structure-based design of transcription factors. Science. Jan. 6, 1995;267(5194):93-6.

Pule et al., A chimeric T cell antigen receptor that augments cytokine release and supports clonal expansion of primary human T cells. Mol Ther. Nov. 2005;12(5):933-41.

Quintarelli et al., Co-expression of cytokine and suicide genes to enhance the activity and safety of tumor-specific cytotoxic T lymphocytes. Blood. Oct. 15, 2007;110(8):2793-802.

Restifo et al., Adoptive immunotherapy for cancer: harnessing the T cell response. Nat Rev Immunol. Mar. 22, 2012;12(4):269-81.

Richards et al., Engineered fibronectin type III domain with a RGDWXE sequence binds with enhanced affinity and specificity to human alphavbeta3 integrin. J Mol Biol. Mar. 7, 2003;326(5):1475-88.

Roux et al., Structural analysis of the nurse shark (new) antigen receptor (NAR): molecular convergence of NAR and unusual mammalian immunoglobulins. Proc Natl Acad Sci U S A. Sep. 29, 1998;95(20):11804-9.

Ryan et al., Virus-encoded proteinases of the picornavirus supergroup. J Gen Virol. Apr. 1997;78 ( Pt 4):699-723.

Sato et al., Genes encoding putative natural killer cell C-type lectin receptors in teleostean fishes. Proc Natl Acad Sci U S A. Jun. 24, 2003;100(13):7779-84.

Schlessinger, Cell signaling by receptor tyrosine kinases. Cell. Oct. 13, 2000;103(2):211-25.

Schonfeld et al., An engineered lipocalin specific for CTLA-4 reveals a combining site with structural and conformational features similar to antibodies. Proc Natl Acad Sci U S A. May 19, 2009;106(20):8198-203.

Skerra, Alternative binding proteins: anticalins—harnessing the structural plasticity of the lipocalin ligand pocket to engineer novel binding activities. FEBS J. Jun. 2008;275(11):2677-83.

Spencer et al., Controlling signal transduction with synthetic ligands. Science. Nov. 12, 1993;262(5136):1019-24.

Standaert et al., Molecular cloning and overexpression of the human FK506-binding protein FKBP. Nature. Aug. 16, 1990;346(6285):671-4.

Stephan et al., T cell-encoded CD80 and 4-1BBL induce auto- and transcostimulation, resulting in potent tumor rejection. Nat Med. Dec. 2007;13(12):1440-9.

Stumpp et al., Designing repeat proteins: modular leucine-rich repeat protein libraries based on the mammalian ribonuclease inhibitor family. J Mol Biol. Sep. 12, 2003;332(2):471-87.

Szymczak et al., Correction of multi-gene deficiency in vivo using a single 'self-cleaving' 2A peptide-based retroviral vector. Nat Biotechnol. May 2004;22(5):589-94.

Tal et al., An NCR1-based chimeric receptor endows T-cells with multiple anti-tumor specificities. Oncotarget. Nov. 15, 2014;5(21):10949-58.

Till et al., CD20-specific adoptive immunotherapy for lymphoma using a chimeric antigen receptor with both CD28 and 4-1BB domains: pilot clinical trial results. Blood. Apr. 26, 2012;119(17):3940-50.

(56) References Cited

OTHER PUBLICATIONS

Varadamsetty et al., Designed Armadillo repeat proteins: library generation, characterization and selection of peptide binders with high specificity. J Mol Biol. Nov. 23, 2012;424(1-2):68-87.
Vincke et al., General strategy to humanize a camelid single-domain antibody and identification of a universal humanized nanobody scaffold. J Biol Chem. Jan. 30, 2009;284(5):3273-3284.
Vita et al., Scorpion toxins as natural scaffolds for protein engineering. Proc Natl Acad Sci U S A. Jul. 3, 1995;92(14):6404-8.
Weisel et al., A model for fibrinogen: domains and sequence. Science. Dec. 20, 1985;230(4732):1388-91.
White et al., Comparison of the glycosyl-phosphatidylinositol cleavage/attachment site between mammalian cells and parasitic protozoa. J Cell Sci. Feb. 2000;113 ( Pt 4):721-7.
Wilkie et al., Dual targeting of ErbB2 and MUC1 in breast cancer using chimeric antigen receptors engineered to provide complementary signaling. J Clin Immunol. Oct. 2012;32(5):1059-70.
Zelensky et al., The C-type lectin-like domain superfamily. Febs J. Dec. 2005;272(24):6179-217.
International Search Report and Written Opinion for Application No. PCT/US2019/066241, dated May 5, 2020, 14 pages.

\* cited by examiner

SEQUENCE LISTING

```
<160> NUMBER OF SEQ ID NOS: 46

<210> SEQ ID NO 1
<211> LENGTH: 364
<212> TYPE: PRT
<213> ORGANISM: Homo sapiens

<400> SEQUENCE: 1

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
```

```
            35                  40                  45
Tyr Tyr Asp Lys Asn Ser Pro Val His Gly Tyr Trp Phe Arg Glu Gly
 50                  55                  60
Ala Ile Ile Ser Arg Asp Ser Pro Val Ala Thr Asn Lys Leu Asp Gln
 65                  70                  75                  80
Glu Val Gln Glu Thr Gln Gly Arg Phe Arg Leu Leu Gly Asp Pro
                 85                  90                  95
Ser Arg Asn Asn Cys Ser Leu Ser Ile Val Asp Ala Arg Arg Asp
                100                 105                 110
Asn Gly Ser Tyr Phe Phe Arg Met Glu Arg Gly Ser Thr Lys Tyr Ser
                115                 120                 125
Tyr Lys Ser Pro Gln Leu Ser Val His Val Thr Asp Leu Thr His Arg
130                 135                 140
Pro Lys Ile Leu Ile Pro Gly Thr Leu Glu Pro Gly His Ser Lys Asn
145                 150                 155                 160
Leu Thr Cys Ser Val Ser Trp Ala Cys Glu Gln Gly Thr Pro Pro Ile
                165                 170                 175
Phe Ser Trp Leu Ser Ala Ala Pro Thr Ser Leu Gly Pro Arg Thr Thr
                180                 185                 190
His Ser Ser Val Leu Ile Ile Thr Pro Arg Pro Gln Asp His Gly Thr
                195                 200                 205
Asn Leu Thr Cys Gln Val Lys Phe Ala Gly Ala Gly Val Thr Thr Glu
                210                 215                 220
Arg Thr Ile Gln Leu Asn Val Thr Tyr Val Pro Gln Asn Pro Thr Thr
225                 230                 235                 240
Gly Ile Phe Pro Gly Asp Gly Ser Gly Lys Gln Glu Thr Arg Ala Gly
                245                 250                 255
Val Val His Gly Ala Ile Gly Gly Ala Gly Val Thr Ala Leu Leu Ala
                260                 265                 270
Leu Cys Leu Cys Leu Ile Phe Phe Ile Val Lys Thr His Arg Arg Lys
                275                 280                 285
Ala Ala Arg Thr Ala Val Gly Arg Asn Asp Thr His Pro Thr Thr Gly
                290                 295                 300
Ser Ala Ser Pro Lys His Gln Lys Lys Ser Lys Leu His Gly Pro Thr
305                 310                 315                 320
Glu Thr Ser Ser Cys Ser Gly Ala Ala Pro Thr Val Glu Met Asp Glu
                325                 330                 335
Glu Leu His Tyr Ala Ser Leu Asn Phe His Gly Met Asn Pro Ser Lys
                340                 345                 350
Asp Thr Ser Thr Glu Tyr Ser Glu Val Arg Thr Gln
                355                 360

<210> SEQ ID NO 2
<211> LENGTH: 245
<212> TYPE: PRT
<213> ORGANISM: Artificial Sequence
<220> FEATURE:
<223> OTHER INFORMATION: Made in Lab - anti-CD33 scFv-1 construct

<400> SEQUENCE: 2

Glu Ile Val Leu Thr Gln Ser Pro Gly Ser Leu Ala Val Ser Pro Gly
 1                5                  10                  15
Glu Arg Val Thr Met Ser Cys Lys Ser Ser Gln Ser Val Phe Phe Ser
                 20                  25                  30
Ser Ser Gln Lys Asn Tyr Leu Ala Trp Tyr Gln Gln Ile Pro Gly Gln
```

```
                35                  40                  45
Ser Pro Arg Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Pro Glu Asp Leu Ala Ile Tyr Tyr Cys His Gln
                 85                  90                  95

Tyr Leu Ser Ser Arg Thr Phe Gly Gln Gly Thr Lys Leu Glu Ile Lys
                100                 105                 110

Gly Gly Gly Gly Ser Gly Gly Gly Gly Ser Gly Gly Gly Gly Ser Gln
            115                 120                 125

Val Gln Leu Gln Gln Pro Gly Ala Glu Val Val Lys Pro Gly Ala Ser
        130                 135                 140

Val Lys Met Ser Cys Lys Ala Ser Gly Tyr Thr Phe Thr Ser Tyr Tyr
145                 150                 155                 160

Ile His Trp Ile Lys Gln Thr Pro Gly Gln Gly Leu Glu Trp Val Gly
                165                 170                 175

Val Ile Tyr Pro Gly Asn Asp Asp Ile Ser Tyr Asn Gln Lys Phe Gln
            180                 185                 190

Gly Lys Ala Thr Leu Thr Ala Asp Lys Ser Ser Thr Thr Ala Tyr Met
        195                 200                 205

Gln Leu Ser Ser Leu Thr Ser Glu Asp Ser Ala Val Tyr Tyr Cys Ala
    210                 215                 220

Arg Glu Val Arg Leu Arg Tyr Phe Asp Val Trp Gly Gln Gly Thr Thr
225                 230                 235                 240

Val Thr Val Ser Ser
                245

<210> SEQ ID NO 3
<211> LENGTH: 242
<212> TYPE: PRT
<213> ORGANISM: Artificial Sequence
<220> FEATURE:
<223> OTHER INFORMATION: Made in Lab - anti-CD33 scFv-2 construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
             20                  25                  30

Gly Ile Ser Phe Met Asn Trp Phe Gln Gln Lys Pro Gly Lys Ala Pro
         35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Phe Ala Thr Tyr Tyr Cys Gln Gln Ser Lys
                 85                  90                  95

Glu Val Pro Trp Thr Phe Gly Gln Gly Thr Lys Val Glu Ile Lys Gly
                100                 105                 110

Gly Gly Ser Gly Gly Gly Ser Gly Gly Gly Ser Gln Val
            115                 120                 125

Gln Leu Val Gln Ser Gly Ala Glu Val Lys Lys Pro Gly Ser Ser Val
        130                 135                 140

Lys Val Ser Cys Lys Ala Ser Gly Tyr Thr Phe Thr Asp Tyr Asn Met
```

His Trp Val Arg Gln Ala Pro Gly Gln Gly Leu Glu Trp Ile Gly Tyr
            145                 150                 155                 160

Ile Tyr Pro Tyr Asn Gly Gly Thr Gly Tyr Asn Gln Lys Phe Lys Ser
            165                 170                 175

Lys Ala Thr Ile Thr Ala Asp Glu Ser Thr Asn Thr Ala Tyr Met Glu
            180                 185                 190

Leu Ser Ser Leu Arg Ser Glu Asp Thr Ala Val Tyr Tyr Cys Ala Arg
            195                 200                 205

Gly Arg Pro Ala Met Asp Tyr Trp Gly Gln Gly Thr Leu Val Thr Val
            210                 215                 220

Ser Ser
225         230                 235                 240

<210> SEQ ID NO 4
<211> LENGTH: 737
<212> TYPE: PRT
<213> ORGANISM: Artificial Sequence
<220> FEATURE:
<223> OTHER INFORMATION: Made in Lab - CD33 DARIC-1 fusion protein
      construct

<400> SEQUENCE: 4

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly

```
                260                 265                 270
Lys Gly His Asp Gly Leu Tyr Gln Gly Leu Ser Thr Ala Thr Lys Asp
                275                 280                 285

Thr Tyr Asp Ala Leu His Met Gln Ala Leu Pro Pro Arg Ser Gly Ser
            290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Ile Val Leu Thr Gln Ser
            340                 345                 350

Pro Gly Ser Leu Ala Val Ser Pro Gly Glu Arg Val Thr Met Ser Cys
            355                 360                 365

Lys Ser Ser Gln Ser Val Phe Phe Ser Ser Gln Lys Asn Tyr Leu
            370                 375                 380

Ala Trp Tyr Gln Gln Ile Pro Gly Gln Ser Pro Arg Leu Leu Ile Tyr
385                 390                 395                 400

Trp Ala Ser Thr Arg Glu Ser Gly Val Pro Asp Arg Phe Thr Gly Ser
                405                 410                 415

Gly Ser Gly Thr Asp Phe Thr Leu Thr Ile Ser Ser Val Gln Pro Glu
                420                 425                 430

Asp Leu Ala Ile Tyr Tyr Cys His Gln Tyr Leu Ser Ser Arg Thr Phe
            435                 440                 445

Gly Gln Gly Thr Lys Leu Glu Ile Lys Gly Gly Gly Ser Gly Gly
            450                 455                 460

Gly Gly Ser Gly Gly Gly Ser Gln Val Gln Leu Gln Gln Pro Gly
465                 470                 475                 480

Ala Glu Val Val Lys Pro Gly Ala Ser Val Lys Met Ser Cys Lys Ala
                485                 490                 495

Ser Gly Tyr Thr Phe Thr Ser Tyr Tyr Ile His Trp Ile Lys Gln Thr
            500                 505                 510

Pro Gly Gln Gly Leu Glu Trp Val Gly Val Ile Tyr Pro Gly Asn Asp
            515                 520                 525

Asp Ile Ser Tyr Asn Gln Lys Phe Gln Gly Lys Ala Thr Leu Thr Ala
            530                 535                 540

Asp Lys Ser Ser Thr Thr Ala Tyr Met Gln Leu Ser Ser Leu Thr Ser
545                 550                 555                 560

Glu Asp Ser Ala Val Tyr Tyr Cys Ala Arg Glu Val Arg Leu Arg Tyr
                565                 570                 575

Phe Asp Val Trp Gly Gln Gly Thr Thr Val Thr Val Ser Ser Gly Gly
                580                 585                 590

Gly Gly Ser Gly Val Gln Val Glu Thr Ile Ser Pro Gly Asp Gly Arg
            595                 600                 605

Thr Phe Pro Lys Arg Gly Gln Thr Cys Val Val His Tyr Thr Gly Met
            610                 615                 620

Leu Glu Asp Gly Lys Lys Phe Asp Ser Ser Arg Asp Arg Asn Lys Pro
625                 630                 635                 640

Phe Lys Phe Met Leu Gly Lys Gln Glu Val Ile Arg Gly Trp Glu Glu
                645                 650                 655

Gly Val Ala Gln Met Ser Val Gly Gln Arg Ala Lys Leu Thr Ile Ser
            660                 665                 670

Pro Asp Tyr Ala Tyr Gly Ala Thr Gly His Pro Gly Ile Ile Pro Pro
            675                 680                 685
```

```
His Ala Thr Leu Val Phe Asp Val Glu Leu Leu Lys Leu Glu Gly Gly
            690                 695                 700

Arg Met Ala Leu Ile Val Leu Gly Gly Val Ala Gly Leu Leu Leu Phe
705                 710                 715                 720

Ile Gly Leu Gly Ile Phe Phe Cys Val Arg Cys Arg His Arg Arg
            725                 730                 735

Gln

<210> SEQ ID NO 5
<211> LENGTH: 734
<212> TYPE: PRT
<213> ORGANISM: Artificial Sequence
<220> FEATURE:
<223> OTHER INFORMATION: Made in Lab - CD33 DARIC-2 fusion protein
      construct

<400> SEQUENCE: 5

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300
```

```
Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Asp Ile Gln Met Thr Gln Ser
            340                 345                 350

Pro Ser Ser Leu Ser Ala Ser Val Gly Asp Arg Val Thr Ile Thr Cys
            355                 360                 365

Arg Ala Ser Glu Ser Val Asp Asn Tyr Gly Ile Ser Phe Met Asn Trp
370                 375                 380

Phe Gln Gln Lys Pro Gly Lys Ala Pro Lys Leu Leu Ile Tyr Ala Ala
385                 390                 395                 400

Ser Asn Gln Gly Ser Gly Val Pro Ser Arg Phe Ser Gly Ser Gly Ser
                405                 410                 415

Gly Thr Asp Phe Thr Leu Thr Ile Ser Ser Leu Gln Pro Asp Asp Phe
            420                 425                 430

Ala Thr Tyr Tyr Cys Gln Gln Ser Lys Glu Val Pro Trp Thr Phe Gly
            435                 440                 445

Gln Gly Thr Lys Val Glu Ile Lys Gly Gly Gly Ser Gly Gly Gly
450                 455                 460

Gly Ser Gly Gly Gly Ser Gln Val Gln Leu Val Gln Ser Gly Ala
465                 470                 475                 480

Glu Val Lys Lys Pro Gly Ser Ser Val Lys Val Ser Cys Lys Ala Ser
                485                 490                 495

Gly Tyr Thr Phe Thr Asp Tyr Asn Met His Trp Val Arg Gln Ala Pro
            500                 505                 510

Gly Gln Gly Leu Glu Trp Ile Gly Tyr Ile Tyr Pro Tyr Asn Gly Gly
            515                 520                 525

Thr Gly Tyr Asn Gln Lys Phe Lys Ser Lys Ala Thr Ile Thr Ala Asp
            530                 535                 540

Glu Ser Thr Asn Thr Ala Tyr Met Glu Leu Ser Ser Leu Arg Ser Glu
545                 550                 555                 560

Asp Thr Ala Val Tyr Tyr Cys Ala Arg Gly Arg Pro Ala Met Asp Tyr
                565                 570                 575

Trp Gly Gln Gly Thr Leu Val Thr Val Ser Ser Gly Gly Gly Gly Ser
            580                 585                 590

Gly Val Gln Val Glu Thr Ile Ser Pro Gly Asp Gly Arg Thr Phe Pro
            595                 600                 605

Lys Arg Gly Gln Thr Cys Val Val His Tyr Thr Gly Met Leu Glu Asp
            610                 615                 620

Gly Lys Lys Phe Asp Ser Ser Arg Asp Arg Asn Lys Pro Phe Lys Phe
625                 630                 635                 640

Met Leu Gly Lys Gln Glu Val Ile Arg Gly Trp Glu Glu Gly Val Ala
            645                 650                 655

Gln Met Ser Val Gly Gln Arg Ala Lys Leu Thr Ile Ser Pro Asp Tyr
            660                 665                 670

Ala Tyr Gly Ala Thr Gly His Pro Gly Ile Ile Pro Pro His Ala Thr
            675                 680                 685

Leu Val Phe Asp Val Glu Leu Leu Lys Leu Glu Gly Arg Met Ala
            690                 695                 700

Leu Ile Val Leu Gly Gly Val Ala Gly Leu Leu Leu Phe Ile Gly Leu
705                 710                 715                 720
```

-continued

Gly Ile Phe Phe Cys Val Arg Cys Arg His Arg Arg Gln
                725                 730

<210> SEQ ID NO 6
<211> LENGTH: 769
<212> TYPE: PRT
<213> ORGANISM: Artificial Sequence
<220> FEATURE:
<223> OTHER INFORMATION: Made in Lab - CD33.OX40 DARIC-1 fusion protein
      construct

<400> SEQUENCE: 6

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
        50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
                100                 105                 110

Arg Ile Ser Lys Ala Ser Ala Gly Thr Gly Ser Asp Ile Tyr Ile Trp
            115                 120                 125

Ala Pro Leu Ala Gly Thr Cys Gly Val Leu Leu Leu Ser Leu Val Ile
        130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
                180                 185                 190

Phe Ser Arg Ser Ala Asp Ala Pro Ala Tyr Gln Gln Gly Gln Asn Gln
            195                 200                 205

Leu Tyr Asn Glu Leu Asn Leu Gly Arg Arg Glu Glu Tyr Asp Val Leu
        210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
                260                 265                 270

Lys Gly His Asp Gly Leu Tyr Gln Gly Leu Ser Thr Ala Thr Lys Asp
            275                 280                 285

Thr Tyr Asp Ala Leu His Met Gln Ala Leu Pro Pro Arg Ser Gly Ser
        290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Ile Val Leu Thr Gln Ser
                340                 345                 350

```
Pro Gly Ser Leu Ala Val Ser Pro Gly Glu Arg Val Thr Met Ser Cys
        355                 360                 365

Lys Ser Ser Gln Ser Val Phe Phe Ser Ser Ser Gln Lys Asn Tyr Leu
    370                 375                 380

Ala Trp Tyr Gln Gln Ile Pro Gly Gln Ser Pro Arg Leu Leu Ile Tyr
385                 390                 395                 400

Trp Ala Ser Thr Arg Glu Ser Gly Val Pro Asp Arg Phe Thr Gly Ser
                405                 410                 415

Gly Ser Gly Thr Asp Phe Thr Leu Thr Ile Ser Ser Val Gln Pro Glu
            420                 425                 430

Asp Leu Ala Ile Tyr Tyr Cys His Gln Tyr Leu Ser Ser Arg Thr Phe
        435                 440                 445

Gly Gln Gly Thr Lys Leu Glu Ile Lys Gly Gly Gly Ser Gly Gly
    450                 455                 460

Gly Gly Ser Gly Gly Gly Ser Gln Val Gln Leu Gln Gln Pro Gly
465                 470                 475                 480

Ala Glu Val Val Lys Pro Gly Ala Ser Val Lys Met Ser Cys Lys Ala
                485                 490                 495

Ser Gly Tyr Thr Phe Thr Ser Tyr Tyr Ile His Trp Ile Lys Gln Thr
            500                 505                 510

Pro Gly Gln Gly Leu Glu Trp Val Gly Val Ile Tyr Pro Gly Asn Asp
        515                 520                 525

Asp Ile Ser Tyr Asn Gln Lys Phe Gln Gly Lys Ala Thr Leu Thr Ala
        530                 535                 540

Asp Lys Ser Ser Thr Thr Ala Tyr Met Gln Leu Ser Ser Leu Thr Ser
545                 550                 555                 560

Glu Asp Ser Ala Val Tyr Tyr Cys Ala Arg Glu Val Arg Leu Arg Tyr
                565                 570                 575

Phe Asp Val Trp Gly Gln Gly Thr Thr Val Thr Val Ser Ser Gly Gly
                580                 585                 590

Gly Gly Ser Gly Val Gln Val Glu Thr Ile Ser Pro Gly Asp Gly Arg
            595                 600                 605

Thr Phe Pro Lys Arg Gly Gln Thr Cys Val Val His Tyr Thr Gly Met
        610                 615                 620

Leu Glu Asp Gly Lys Lys Phe Asp Ser Ser Arg Asp Arg Asn Lys Pro
625                 630                 635                 640

Phe Lys Phe Met Leu Gly Lys Gln Glu Val Ile Arg Gly Trp Glu Glu
                645                 650                 655

Gly Val Ala Gln Met Ser Val Gly Gln Arg Ala Lys Leu Thr Ile Ser
            660                 665                 670

Pro Asp Tyr Ala Tyr Gly Ala Thr Gly His Pro Gly Ile Ile Pro Pro
        675                 680                 685

His Ala Thr Leu Val Phe Asp Val Glu Leu Leu Lys Leu Glu Gly Gly
        690                 695                 700

Arg Met Ala Leu Ile Val Leu Gly Val Ala Gly Leu Leu Leu Phe
705                 710                 715                 720

Ile Gly Leu Gly Ile Phe Phe Ala Leu Tyr Leu Leu Arg Arg Asp Gln
                725                 730                 735

Arg Leu Pro Pro Asp Ala His Lys Pro Pro Gly Gly Gly Ser Phe Arg
            740                 745                 750

Thr Pro Ile Gln Glu Glu Gln Ala Asp Ala His Ser Thr Leu Ala Lys
        755                 760                 765
```

Ile

```
<210> SEQ ID NO 7
<211> LENGTH: 766
<212> TYPE: PRT
<213> ORGANISM: Artificial Sequence
<220> FEATURE:
<223> OTHER INFORMATION: Made in Lab - CD33.OX40 DARIC-2 fusion protein

<400> SEQUENCE: 7
```

| | | | | | | | | | | | | | | |
|---|---|---|---|---|---|---|---|---|---|---|---|---|---|---|
| Met | Ala | Leu | Pro | Val | Thr | Ala | Leu | Leu | Pro | Leu | Ala | Leu | Leu | Leu |
| 1 | | | | 5 | | | | | 10 | | | | | 15 |
| His | Ala | Ala | Arg | Pro | Gly | Ser | Ile | Leu | Trp | His | Glu | Met | Trp | His |
| | | | 20 | | | | | 25 | | | | | 30 | |
| Glu | Gly | Leu | Glu | Glu | Ala | Ser | Arg | Leu | Tyr | Phe | Gly | Glu | Arg | Asn |
| | | | | 35 | | | | | 40 | | | | | 45 |
| Val | Lys | Gly | Met | Phe | Glu | Val | Leu | Glu | Pro | Leu | His | Ala | Met | Met |
| | | 50 | | | | | 55 | | | | | 60 | | |
| Glu | Arg | Gly | Pro | Gln | Thr | Leu | Lys | Glu | Thr | Ser | Phe | Asn | Gln | Ala |
| 65 | | | | | 70 | | | | | 75 | | | | | 80 |
| Tyr | Gly | Arg | Asp | Leu | Met | Glu | Ala | Gln | Glu | Trp | Cys | Arg | Lys | Tyr |
| | | | | 85 | | | | | 90 | | | | | 95 |
| Met | Lys | Ser | Gly | Asn | Val | Lys | Asp | Leu | Leu | Gln | Ala | Trp | Asp | Leu |
| | | | 100 | | | | | 105 | | | | | 110 | |
| Tyr | Tyr | His | Val | Phe | Arg | Arg | Ile | Ser | Lys | Ala | Ser | Ala | Gly | Thr |
| | | | | 115 | | | | | 120 | | | | | 125 |
| Gly | Ser | Asp | Ile | Tyr | Ile | Trp | Ala | Pro | Leu | Ala | Gly | Thr | Cys | Gly |
| | | 130 | | | | | 135 | | | | | 140 | | |
| Val | Leu | Leu | Leu | Ser | Leu | Val | Ile | Thr | Met | His | Lys | Arg | Gly | Arg |
| 145 | | | | | 150 | | | | | 155 | | | | | 160 |
| Lys | Lys | Leu | Leu | Tyr | Ile | Phe | Lys | Gln | Pro | Phe | Met | Arg | Pro | Val |
| | | | | 165 | | | | | 170 | | | | | 175 |
| Gln | Thr | Thr | Gln | Glu | Asp | Gly | Cys | Ser | Cys | Arg | Phe | Pro | Glu | Glu |
| | | | 180 | | | | | 185 | | | | | 190 | |
| Glu | Glu | Gly | Gly | Cys | Glu | Leu | Arg | Val | Lys | Phe | Ser | Arg | Ser | Ala |
| | | | | 195 | | | | | 200 | | | | | 205 |
| Asp | Ala | Pro | Ala | Tyr | Gln | Gln | Gly | Gln | Asn | Gln | Leu | Tyr | Asn | Glu |
| | | 210 | | | | | 215 | | | | | 220 | | |
| Leu | Asn | Leu | Gly | Arg | Arg | Glu | Glu | Tyr | Asp | Val | Leu | Asp | Lys | Arg |
| 225 | | | | | 230 | | | | | 235 | | | | | 240 |
| Arg | Gly | Arg | Asp | Pro | Glu | Met | Gly | Gly | Lys | Pro | Arg | Arg | Lys | Asn |
| | | | | 245 | | | | | 250 | | | | | 255 |
| Pro | Gln | Glu | Gly | Leu | Tyr | Asn | Glu | Leu | Gln | Lys | Asp | Lys | Met | Ala |
| | | | 260 | | | | | 265 | | | | | 270 | |
| Glu | Ala | Tyr | Ser | Glu | Ile | Gly | Met | Lys | Gly | Glu | Arg | Arg | Arg | Gly |
| | | | | 275 | | | | | 280 | | | | | 285 |
| Lys | Gly | His | Asp | Gly | Leu | Tyr | Gln | Gly | Leu | Ser | Thr | Ala | Thr | Lys |
| | | 290 | | | | | 295 | | | | | 300 | | |
| Asp | Thr | Tyr | Asp | Ala | Leu | His | Met | Gln | Ala | Leu | Pro | Pro | Arg | Ser |
| 305 | | | | | 310 | | | | | 315 | | | | | 320 |
| Gly | Ser | Gly | Ala | Thr | Asn | Phe | Ser | Leu | Leu | Lys | Gln | Ala | Gly | Asp |
| | | | | 325 | | | | | 330 | | | | | 335 |
| Val | Glu | Glu | Asn | Pro | Gly | Pro | Ser | Met | Glu | Thr | Asp | Thr | Leu | Leu |
| | | | 340 | | | | | 345 | | | | | 350 | |
| Leu | Trp | Val | Leu | Leu | Leu | Trp | Val | Pro | Gly | Ser | Thr | Gly | Asp | Ile |

Gln Met Thr Gln Ser Pro Ser Ser Leu Ser Ala Ser Val Gly Asp Arg Val Thr Ile Thr Cys

-continued

```
            355                 360                 365
Arg Ala Ser Glu Ser Val Asp Asn Tyr Gly Ile Ser Phe Met Asn Trp
    370                 375                 380

Phe Gln Gln Lys Pro Gly Lys Ala Pro Lys Leu Leu Ile Tyr Ala Ala
385                 390                 395                 400

Ser Asn Gln Gly Ser Gly Val Pro Ser Arg Phe Ser Gly Ser Gly Ser
                405                 410                 415

Gly Thr Asp Phe Thr Leu Thr Ile Ser Ser Leu Gln Pro Asp Asp Phe
            420                 425                 430

Ala Thr Tyr Tyr Cys Gln Gln Ser Lys Glu Val Pro Trp Thr Phe Gly
        435                 440                 445

Gln Gly Thr Lys Val Glu Ile Lys Gly Gly Gly Ser Gly Gly Gly
    450                 455                 460

Gly Ser Gly Gly Gly Ser Gln Val Gln Leu Val Gln Ser Gly Ala
465                 470                 475                 480

Glu Val Lys Lys Pro Gly Ser Ser Val Lys Val Ser Cys Lys Ala Ser
                485                 490                 495

Gly Tyr Thr Phe Thr Asp Tyr Asn Met His Trp Val Arg Gln Ala Pro
            500                 505                 510

Gly Gln Gly Leu Glu Trp Ile Gly Tyr Ile Tyr Pro Tyr Asn Gly Gly
        515                 520                 525

Thr Gly Tyr Asn Gln Lys Phe Lys Ser Lys Ala Thr Ile Thr Ala Asp
    530                 535                 540

Glu Ser Thr Asn Thr Ala Tyr Met Glu Leu Ser Ser Leu Arg Ser Glu
545                 550                 555                 560

Asp Thr Ala Val Tyr Tyr Cys Ala Arg Gly Arg Pro Ala Met Asp Tyr
                565                 570                 575

Trp Gly Gln Gly Thr Leu Val Thr Val Ser Ser Gly Gly Gly Gly Ser
            580                 585                 590

Gly Val Gln Val Glu Thr Ile Ser Pro Gly Asp Gly Arg Thr Phe Pro
        595                 600                 605

Lys Arg Gly Gln Thr Cys Val Val His Tyr Thr Gly Met Leu Glu Asp
    610                 615                 620

Gly Lys Lys Phe Asp Ser Ser Arg Asp Arg Asn Lys Pro Phe Lys Phe
625                 630                 635                 640

Met Leu Gly Lys Gln Glu Val Ile Arg Gly Trp Glu Glu Gly Val Ala
                645                 650                 655

Gln Met Ser Val Gly Gln Arg Ala Lys Leu Thr Ile Ser Pro Asp Tyr
            660                 665                 670

Ala Tyr Gly Ala Thr Gly His Pro Gly Ile Ile Pro Pro His Ala Thr
        675                 680                 685

Leu Val Phe Asp Val Glu Leu Leu Lys Leu Glu Gly Gly Arg Met Ala
    690                 695                 700

Leu Ile Val Leu Gly Gly Val Ala Gly Leu Leu Leu Phe Ile Gly Leu
705                 710                 715                 720

Gly Ile Phe Phe Ala Leu Tyr Leu Leu Arg Arg Asp Gln Arg Leu Pro
                725                 730                 735

Pro Asp Ala His Lys Pro Pro Gly Gly Gly Ser Phe Arg Thr Pro Ile
            740                 745                 750

Gln Glu Glu Gln Ala Asp Ala His Ser Thr Leu Ala Lys Ile
        755                 760                 765
```

<210> SEQ ID NO 8

```
<211> LENGTH: 901
<212> TYPE: PRT
<213> ORGANISM: Artificial Sequence
<220> FEATURE:
<223> OTHER INFORMATION: Made in Lab - CD33.TNFR2 DARIC-1 fusion protein
      construct

<400> SEQUENCE: 8
```

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Ile Val Leu Thr Gln Ser
            340                 345                 350

Pro Gly Ser Leu Ala Val Ser Pro Gly Glu Arg Val Thr Met Ser Cys
        355                 360                 365

Lys Ser Ser Gln Ser Val Phe Phe Ser Ser Ser Gln Lys Asn Tyr Leu

```
            370                 375                 380
Ala Trp Tyr Gln Gln Ile Pro Gly Gln Ser Pro Arg Leu Leu Ile Tyr
385                 390                 395                 400

Trp Ala Ser Thr Arg Glu Ser Gly Val Pro Asp Arg Phe Thr Gly Ser
                405                 410                 415

Gly Ser Gly Thr Asp Phe Thr Leu Thr Ile Ser Ser Val Gln Pro Glu
                420                 425                 430

Asp Leu Ala Ile Tyr Tyr Cys His Gln Tyr Leu Ser Ser Arg Thr Phe
            435                 440                 445

Gly Gln Gly Thr Lys Leu Glu Ile Lys Gly Gly Gly Ser Gly Gly
        450                 455                 460

Gly Gly Ser Gly Gly Gly Ser Gln Val Gln Leu Gln Gln Pro Gly
465                 470                 475                 480

Ala Glu Val Val Lys Pro Gly Ala Ser Val Lys Met Ser Cys Lys Ala
                485                 490                 495

Ser Gly Tyr Thr Phe Thr Ser Tyr Tyr Ile His Trp Ile Lys Gln Thr
                500                 505                 510

Pro Gly Gln Gly Leu Glu Trp Val Gly Val Ile Tyr Pro Gly Asn Asp
            515                 520                 525

Asp Ile Ser Tyr Asn Gln Lys Phe Gln Gly Lys Ala Thr Leu Thr Ala
        530                 535                 540

Asp Lys Ser Ser Thr Thr Ala Tyr Met Gln Leu Ser Ser Leu Thr Ser
545                 550                 555                 560

Glu Asp Ser Ala Val Tyr Tyr Cys Ala Arg Glu Val Arg Leu Arg Tyr
                565                 570                 575

Phe Asp Val Trp Gly Gln Gly Thr Thr Val Thr Val Ser Ser Gly Gly
            580                 585                 590

Gly Gly Ser Gly Val Gln Val Glu Thr Ile Ser Pro Gly Asp Gly Arg
        595                 600                 605

Thr Phe Pro Lys Arg Gly Gln Thr Cys Val Val His Tyr Thr Gly Met
        610                 615                 620

Leu Glu Asp Gly Lys Lys Phe Asp Ser Ser Arg Asp Arg Asn Lys Pro
625                 630                 635                 640

Phe Lys Phe Met Leu Gly Lys Gln Glu Val Ile Arg Gly Trp Glu Glu
                645                 650                 655

Gly Val Ala Gln Met Ser Val Gly Gln Arg Ala Lys Leu Thr Ile Ser
                660                 665                 670

Pro Asp Tyr Ala Tyr Gly Ala Thr Gly His Pro Gly Ile Ile Pro Pro
            675                 680                 685

His Ala Thr Leu Val Phe Asp Val Glu Leu Leu Lys Leu Glu Gly Gly
        690                 695                 700

Arg Met Ala Leu Ile Val Leu Gly Gly Val Ala Gly Leu Leu Leu Phe
705                 710                 715                 720

Ile Gly Leu Gly Ile Phe Phe Lys Lys Pro Leu Cys Leu Gln Arg
                725                 730                 735

Glu Ala Lys Val Pro His Leu Pro Ala Asp Lys Ala Arg Gly Thr Gln
                740                 745                 750

Gly Pro Glu Gln Gln His Leu Leu Ile Thr Ala Pro Ser Ser Ser
            755                 760                 765

Ser Ser Leu Glu Ser Ser Ala Ser Ala Leu Asp Arg Arg Ala Pro Thr
        770                 775                 780

Arg Asn Gln Pro Gln Ala Pro Gly Val Glu Ala Ser Gly Ala Gly Glu
785                 790                 795                 800
```

```
Ala Arg Ala Ser Thr Gly Ser Ser Asp Ser Ser Pro Gly Gly His Gly
                805                 810                 815

Thr Gln Val Asn Val Thr Cys Ile Val Asn Val Cys Ser Ser Ser Asp
            820                 825                 830

His Ser Ser Gln Cys Ser Ser Gln Ala Ser Ser Thr Met Gly Asp Thr
            835                 840                 845

Asp Ser Ser Pro Ser Glu Ser Pro Lys Asp Glu Gln Val Pro Phe Ser
850                 855                 860

Lys Glu Glu Cys Ala Phe Arg Ser Gln Leu Glu Thr Pro Glu Thr Leu
865                 870                 875                 880

Leu Gly Ser Thr Glu Glu Lys Pro Leu Pro Leu Gly Val Pro Asp Ala
            885                 890                 895

Gly Met Lys Pro Ser
            900

<210> SEQ ID NO 9
<211> LENGTH: 898
<212> TYPE: PRT
<213> ORGANISM: Artificial Sequence
<220> FEATURE:
<223> OTHER INFORMATION: Made in Lab - CD33.TNFR2 DARIC-2 fusion protein
      construct

<400> SEQUENCE: 9

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
```

-continued

```
                245                 250                 255
Ala Glu Ala Tyr Ser Glu Ile Gly Met Lys Gly Glu Arg Arg Gly
            260                 265                 270
Lys Gly His Asp Gly Leu Tyr Gln Gly Leu Ser Thr Ala Thr Lys Asp
        275                 280                 285
Thr Tyr Asp Ala Leu His Met Gln Ala Leu Pro Pro Arg Ser Gly Ser
    290                 295                 300
Gly Ala Thr Asn Phe Ser Leu Leu Lys Gln Ala Gly Asp Val Glu Glu
305                 310                 315                 320
Asn Pro Gly Pro Ser Met Glu Thr Asp Thr Leu Leu Leu Trp Val Leu
                325                 330                 335
Leu Leu Trp Val Pro Gly Ser Thr Gly Asp Ile Gln Met Thr Gln Ser
            340                 345                 350
Pro Ser Ser Leu Ser Ala Ser Val Gly Asp Arg Val Thr Ile Thr Cys
        355                 360                 365
Arg Ala Ser Glu Ser Val Asp Asn Tyr Gly Ile Ser Phe Met Asn Trp
    370                 375                 380
Phe Gln Gln Lys Pro Gly Lys Ala Pro Lys Leu Leu Ile Tyr Ala Ala
385                 390                 395                 400
Ser Asn Gln Gly Ser Gly Val Pro Ser Arg Phe Ser Gly Ser Gly Ser
                405                 410                 415
Gly Thr Asp Phe Thr Leu Thr Ile Ser Ser Leu Gln Pro Asp Asp Phe
            420                 425                 430
Ala Thr Tyr Tyr Cys Gln Gln Ser Lys Glu Val Pro Trp Thr Phe Gly
        435                 440                 445
Gln Gly Thr Lys Val Glu Ile Lys Gly Gly Gly Ser Gly Gly Gly
    450                 455                 460
Gly Ser Gly Gly Gly Ser Gln Val Gln Leu Val Gln Ser Gly Ala
465                 470                 475                 480
Glu Val Lys Lys Pro Gly Ser Ser Val Lys Val Ser Cys Lys Ala Ser
                485                 490                 495
Gly Tyr Thr Phe Thr Asp Tyr Asn Met His Trp Val Arg Gln Ala Pro
            500                 505                 510
Gly Gln Gly Leu Glu Trp Ile Gly Tyr Ile Tyr Pro Tyr Asn Gly Gly
        515                 520                 525
Thr Gly Tyr Asn Gln Lys Phe Lys Ser Lys Ala Thr Ile Thr Ala Asp
    530                 535                 540
Glu Ser Thr Asn Thr Ala Tyr Met Glu Leu Ser Ser Leu Arg Ser Glu
545                 550                 555                 560
Asp Thr Ala Val Tyr Tyr Cys Ala Arg Gly Arg Pro Ala Met Asp Tyr
                565                 570                 575
Trp Gly Gln Gly Thr Leu Val Thr Val Ser Ser Gly Gly Gly Gly Ser
            580                 585                 590
Gly Val Gln Val Glu Thr Ile Ser Pro Gly Asp Gly Arg Thr Phe Pro
        595                 600                 605
Lys Arg Gly Gln Thr Cys Val Val His Tyr Thr Gly Met Leu Glu Asp
    610                 615                 620
Gly Lys Lys Phe Asp Ser Ser Arg Asp Arg Asn Lys Pro Phe Lys Phe
625                 630                 635                 640
Met Leu Gly Lys Gln Glu Val Ile Arg Gly Trp Glu Glu Gly Val Ala
                645                 650                 655
Gln Met Ser Val Gly Gln Arg Ala Lys Leu Thr Ile Ser Pro Asp Tyr
            660                 665                 670
```

```
Ala Tyr Gly Ala Thr Gly His Pro Gly Ile Ile Pro Pro His Ala Thr
            675                 680                 685

Leu Val Phe Asp Val Glu Leu Leu Lys Leu Glu Gly Gly Arg Met Ala
        690                 695                 700

Leu Ile Val Leu Gly Gly Val Ala Gly Leu Leu Leu Phe Ile Gly Leu
705                 710                 715                 720

Gly Ile Phe Phe Lys Lys Pro Leu Cys Leu Gln Arg Glu Ala Lys
                725                 730                 735

Val Pro His Leu Pro Ala Asp Lys Ala Arg Gly Thr Gln Gly Pro Glu
                740                 745                 750

Gln Gln His Leu Leu Ile Thr Ala Pro Ser Ser Ser Ser Ser Ser Leu
            755                 760                 765

Glu Ser Ser Ala Ser Ala Leu Asp Arg Arg Ala Pro Thr Arg Asn Gln
        770                 775                 780

Pro Gln Ala Pro Gly Val Glu Ala Ser Gly Ala Gly Glu Ala Arg Ala
785                 790                 795                 800

Ser Thr Gly Ser Ser Asp Ser Ser Pro Gly Gly His Gly Thr Gln Val
                805                 810                 815

Asn Val Thr Cys Ile Val Asn Val Cys Ser Ser Asp His Ser Ser
                820                 825                 830

Gln Cys Ser Ser Gln Ala Ser Ser Thr Met Gly Asp Thr Asp Ser Ser
        835                 840                 845

Pro Ser Glu Ser Pro Lys Asp Glu Gln Val Pro Phe Ser Lys Glu Glu
850                 855                 860

Cys Ala Phe Arg Ser Gln Leu Glu Thr Pro Glu Thr Leu Leu Gly Ser
865                 870                 875                 880

Thr Glu Glu Lys Pro Leu Pro Leu Gly Val Pro Asp Ala Gly Met Lys
                885                 890                 895

Pro Ser

<210> SEQ ID NO 10
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 10

Asp Gly Gly Gly Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 11

Thr Gly Glu Lys Pro
1               5

<210> SEQ ID NO 12
<211> LENGTH: 4
<212> TYPE: PRT
<213> ORGANISM: Artificial Sequence
<220> FEATURE:
<223> OTHER INFORMATION: Exemplary linker sequence
```

```
<400> SEQUENCE: 12

Gly Gly Arg Arg
1

<210> SEQ ID NO 13
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 13

Gly Gly Gly Gly Ser
1               5

<210> SEQ ID NO 14
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 14

Glu Gly Lys Ser Ser Gly Ser Gly Ser Glu Ser Lys Val Asp
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 15

Lys Glu Ser Gly Ser Val Ser Ser Glu Gln Leu Ala Gln Phe Arg Ser
1               5                   10                  15

Leu Asp

<210> SEQ ID NO 16
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 16

Gly Gly Arg Arg Gly Gly Gly Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 17

Leu Arg Gln Arg Asp Gly Glu Arg Pro
1               5

<210> SEQ ID NO 18
<211> LENGTH: 12
<212> TYPE: PRT
<213> ORGANISM: Artificial Sequence
<220> FEATURE:
<223> OTHER INFORMATION: Exemplary linker sequence
```

```
<400> SEQUENCE: 18

Leu Arg Gln Lys Asp Gly Gly Gly Ser Glu Arg Pro
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 19

Leu Arg Gln Lys Asp Gly Gly Gly Ser Gly Gly Gly Ser Glu Arg Pro
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 20

Gly Ser Thr Ser Gly Ser Gly Lys Pro Gly Ser Gly Glu Gly Ser Thr
1               5                   10                  15

Lys Gly

<210> SEQ ID NO 21
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 21

Glu Xaa Xaa Tyr Xaa Gln Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 22

Glu Asn Leu Tyr Phe Gln Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Cleavage sequence by TEV protease
```

```
<400> SEQUENCE: 23

Glu Asn Leu Tyr Phe Gln Ser
1               5

<210> SEQ ID NO 24
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 24

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 25
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 25

Ala Thr Asn Phe Ser Leu Leu Lys Gln Ala Gly Asp Val Glu Glu Asn
1               5                   10                  15

Pro Gly Pro

<210> SEQ ID NO 26
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 26

Leu Leu Lys Gln Ala Gly Asp Val Glu Glu Asn Pro Gly Pro
1               5                   10

<210> SEQ ID NO 27
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 27

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 28
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 28

Glu Gly Arg Gly Ser Leu Leu Thr Cys Gly Asp Val Glu Glu Asn Pro
1               5                   10                  15
```

Gly Pro

<210> SEQ ID NO 29
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 29

Leu Leu Thr Cys Gly Asp Val Glu Glu Asn Pro Gly Pro
1               5                   10

<210> SEQ ID NO 30
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 30

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 31
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 31

Gln Cys Thr Asn Tyr Ala Leu Leu Lys Leu Ala Gly Asp Val Glu Ser
1               5                   10                  15

Asn Pro Gly Pro
            20

<210> SEQ ID NO 32
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 32

Leu Leu Lys Leu Ala Gly Asp Val Glu Ser Asn Pro Gly Pro
1               5                   10

<210> SEQ ID NO 33
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 33

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 34
<211> LENGTH: 22

```
<212> TYPE: PRT
<213> ORGANISM: Artificial Sequence
<220> FEATURE:
<223> OTHER INFORMATION: Self-cleaving polypeptide comprising 2A site

<400> SEQUENCE: 34

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 35
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Leu Leu Lys Leu Ala Gly Asp Val Glu Ser Asn Pro Gly Pro
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 36

Leu Leu Asn Phe Asp Leu Leu Lys Leu Ala Gly Asp Val Glu Ser Asn
1               5                   10                  15

Pro Gly Pro

<210> SEQ ID NO 37
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Thr Leu Asn Phe Asp Leu Leu Lys Leu Ala Gly Asp Val Glu Ser Asn
1               5                   10                  15

Pro Gly Pro

<210> SEQ ID NO 38
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Leu Leu Lys Leu Ala Gly Asp Val Glu Ser Asn Pro Gly Pro
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 39
```

```
Asn Phe Asp Leu Leu Lys Leu Ala Gly Asp Val Glu Ser Asn Pro Gly
1               5                   10                  15

Pro

<210> SEQ ID NO 40
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Gln Leu Leu Asn Phe Asp Leu Leu Lys Leu Ala Gly Asp Val Glu Ser
1               5                   10                  15

Asn Pro Gly Pro
            20

<210> SEQ ID NO 41
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 42
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 43
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 43

Leu Asn Phe Asp Leu Leu Lys Leu Ala Gly Asp Val Glu Ser Asn Pro
1               5                   10                  15

Gly Pro

<210> SEQ ID NO 44
<211> LENGTH: 40
<212> TYPE: PRT
<213> ORGANISM: Artificial Sequence
<220> FEATURE:
<223> OTHER INFORMATION: Self-cleaving polypeptide comprising 2A site
```

```
<400> SEQUENCE: 44

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
                20                  25                  30

Asp Val Glu Ser Asn Pro Gly Pro
            35              40

<210> SEQ ID NO 45
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 45

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
                20                  25                  30

Pro

<210> SEQ ID NO 46
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 46 gccrccatgg                                                                10
```

DIMERIZING AGENT REGULATED IMMUNORECEPTOR COMPLEXES

CROSS REFERENCE TO RELATED APPLICATIONS

This application is a National Stage application under 35 U.S.C. § 371 of International Application No. PCT/US2019/066241, filed Dec. 13, 2019, which claims the benefit under 35 U.S.C. § 119 (e) of U.S. Provisional Application No. 62/835,662, filed Apr. 18, 2019, and U.S. Provisional Application No. 62/779,953, filed Dec. 14, 2018, where these applications are herein incorporated by reference in their entireties.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLBD_114_02WO_ST25.txt. The text file is 59 KB, was created on Dec. 11, 2019, and is being submitted electronically via EFS-Web, concurrent with the filing of the specification.

BACKGROUND

Technical Field

The present disclosure relates to improved adoptive cell therapies. More particularly, the disclosure relates to improved chemically regulated signaling molecules, cells, and methods of using the same for modulating spatial and temporal control of cellular signal initiation and downstream responses during adoptive immunotherapy.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

Adoptive cellular therapy is emerging as a powerful paradigm for delivering complex biological signals to treat cancer. In contrast to small molecule and biologic drug compositions, adoptive cell therapies have the potential to execute unique therapeutic tasks owing to their myriad sensory and response programs and increasingly defined mechanisms of genetic control. To achieve such therapeutic value, cells need to be outfitted with machinery for sensing and integrating chemical and/or biological information associated with local physiological environments.

BRIEF SUMMARY

The present disclosure generally relates, in part, to dimerizing agent regulated immunoreceptor complexes (DARICs) that recognize CD33, and optionally another target antigen, polynucleotides and polypeptides encoding the same, compositions thereof, and methods of making and using the same to treat cancer.

In various embodiments, a non-natural cell comprises a first polypeptide comprising: an FRB multimerization domain polypeptide or variant thereof; a CD8α transmembrane domain or a CD4 transmembrane domain; a CD137 co-stimulatory domain; and/or a CD3 ζ primary signaling domain; and a second polypeptide comprising: a binding domain that binds to CD33; an FKBP multimerization domain polypeptide or variant thereof; and a CD4 transmembrane domain or a CD8α transmembrane domain; wherein a bridging factor promotes the formation of a polypeptide complex on the non-natural cell surface with the bridging factor associated with and disposed between the multimerization domains of the first and second polypeptides.

In certain embodiments, the FKBP multimerization domain is FKBP12.

In further embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In various embodiments, the first polypeptide comprises a CD8α transmembrane domain; a CD137 co-stimulatory domain; and a CD3 ζ primary signaling domain.

In some embodiments, the second polypeptide comprises a CD4 transmembrane domain.

In certain embodiments, the binding domain comprises an antibody or antigen binding fragment thereof.

In various embodiments, the antibody or antigen binding fragment thereof is selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In additional embodiments, the binding domain comprises an antibody or antigen binding fragment thereof that competes with the amino acid sequence set forth in SEQ ID NO: 2 or 3, for binding to CD33.

In some embodiments, the binding domain comprises the amino acid sequence set forth in SEQ ID NO: 2 or 3.

In various embodiments, the second polypeptide comprises a costimulatory domain.

In particular embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNFRS25, and zeta chain of T cell receptor associated protein kinase 70 (ZAP70).

In certain embodiments, the costimulatory domain of the second polypeptide is a costimulatory domain isolated from OX40 or TNFR2.

In further embodiments, a non-natural cell comprises a polypeptide complex that comprises a first polypeptide comprising: an FRB multimerization domain polypeptide or variant thereof; a CD8α transmembrane domain or a CD4 transmembrane domain; a CD137 co-stimulatory domain; and/or a CD3 ζ primary signaling domain; a second polypeptide comprising: a binding domain that binds to CD33; an FKBP multimerization domain polypeptide or variant thereof; and a CD4 transmembrane domain or a CD8α transmembrane domain; and a bridging factor associated with and disposed between the multimerization domains of the first and second polypeptides.

In various embodiments, the FKBP multimerization domain is FKBP12.

In particular embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a CD8α transmembrane domain; a CD137 co-stimulatory domain; and a CD3 ζ primary signaling domain.

In certain embodiments, the second polypeptide comprises a CD4 transmembrane domain.

In various embodiments, the binding domain comprises an antibody or antigen binding fragment thereof.

In some embodiments, the antibody or antigen binding fragment thereof is selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In particular embodiments, the binding domain comprises an antibody or antigen binding fragment thereof that competes with the amino acid sequence set forth in SEQ ID NO: 2 or 3, for binding to CD33.

In some embodiments, the binding domain comprises the amino acid sequence set forth in SEQ ID NO: 2 or 3.

In various embodiments, the second polypeptide comprises a costimulatory domain.

In additional embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In particular embodiments, the costimulatory domain of the second polypeptide is a costimulatory domain isolated from OX40 or TNFR2.

In particular embodiments, the cell is a hematopoietic cell.

In certain embodiments, the cell is a T cell.

In various embodiments, the cell is a CD3+, CD4+, and/or CD8+ cell.

In some embodiments, the cell is an immune effector cell.

In further embodiments, the cell is a cytotoxic T lymphocytes (CTLs), a tumor infiltrating lymphocytes (TILs), or a helper T cell.

In various embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In additional embodiments, the FRB multimerization domain and the FKBP multimerization domain localize extracellularly when of the first polypeptide and the second polypeptide are expressed.

In certain embodiments, a fusion polypeptide comprises a first polypeptide comprising: an FRB multimerization domain polypeptide or variant thereof; a CD8α transmembrane domain or a CD4 transmembrane domain; a CD137 co-stimulatory domain; and/or a CD3 ζ primary signaling domain; a polypeptide cleavage signal; and a second polypeptide comprising: a binding domain that binds to CD33; an FKBP multimerization domain polypeptide or variant thereof; and a CD4 transmembrane domain or a CD8α transmembrane domain.

In various embodiments, the FKBP multimerization domain is FKBP12.

In some embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In some embodiments, the first polypeptide comprises a CD8α transmembrane domain; a CD137 co-stimulatory domain; and a CD3 ζ primary signaling domain.

In certain embodiments, the second polypeptide comprises a CD4 transmembrane domain.

In various embodiments, the binding domain comprises an antibody or antigen binding fragment thereof.

In additional embodiments, the antibody or antigen binding fragment thereof is selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In particular embodiments, the binding domain comprises an antibody or antigen binding fragment thereof that competes with the amino acid sequence set forth in SEQ ID NO: 2 or 3, for binding to CD33.

In some embodiments, the binding domain comprises the amino acid sequence set forth in SEQ ID NO: 2 or 3.

In various embodiments, the second polypeptide comprises a costimulatory domain.

In some embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In particular embodiments, the costimulatory domain of the second polypeptide is a costimulatory domain isolated from OX40 or TNFR2.

In certain embodiments, the polypeptide cleavage signal is a viral self-cleaving polypeptide.

In various embodiments, the polypeptide cleavage signal is a viral self-cleaving 2A polypeptide.

In additional embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In some embodiments, the FRB multimerization domain and the FKBP multimerization domain localize extracellularly when of the first polypeptide and the second polypeptide are expressed.

In various embodiments, a polypeptide complex comprises a first polypeptide comprising: an FRB multimerization domain polypeptide or variant thereof; a CD8α transmembrane domain or a CD4 transmembrane domain; a CD137 co-stimulatory domain; and/or a CD3 ζ primary signaling domain; a second polypeptide comprising: a binding domain that binds to CD33 2; an FKBP multimerization domain polypeptide or variant thereof; and a CD4 transmembrane domain or a CD8α transmembrane domain; and a bridging factor associated with and disposed between the multimerization domains of the first and second polypeptides.

In some embodiments, the FKBP multimerization domain is FKBP12.

In certain embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a CD8α transmembrane domain; a CD137 co-stimulatory domain; and a CD3 ζ primary signaling domain.

In various embodiments, the second polypeptide comprises a CD4 transmembrane domain.

In particular embodiments, the binding domain comprises an antibody or antigen binding fragment thereof.

In some embodiments, the antibody or antigen binding fragment thereof is selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In various embodiments, the binding domain comprises an antibody or antigen binding fragment thereof that competes with the amino acid sequence set forth in SEQ ID NO: 2 or 3, for binding to CD33.

In some embodiments, the binding domain comprises the amino acid sequence set forth in SEQ ID NO: 2 or 3.

In particular embodiments, the second polypeptide comprises a costimulatory domain.

In certain embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In various embodiments, the costimulatory domain of the second polypeptide is a costimulatory domain isolated from OX40 or TNFR2.

In additional embodiments, the cell is a hematopoietic cell.

In particular embodiments, the cell is a T cell.

In further embodiments, the cell is a CD3+, CD4+, and/or CD8+ cell.

In some embodiments, the cell is an immune effector cell.

In certain embodiments, the cell is a cytotoxic T lymphocytes (CTLs), a tumor infiltrating lymphocytes (TILs), or a helper T cell.

In various embodiments, the cell is a natural killer (NK) cell or natural killer T (NKT) cell.

In additional embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the FRB multimerization domain and the FKBP multimerization domain localize extracellularly when of the first polypeptide and the second polypeptide are expressed.

In various embodiments, a non-natural cell comprises: a first polypeptide comprising an FRB multimerization domain polypeptide or variant thereof, a CD8α transmembrane domain or a CD4 transmembrane domain, a CD137 co-stimulatory domain, and/or a CD3 ζ primary signaling domain; a second polypeptide comprising a binding domain that binds to CD33, an FKBP multimerization domain polypeptide or variant thereof, and a CD4 transmembrane domain or a CD8α transmembrane domain; and a third polypeptide comprising a binding domain that binds to another target antigen, an FK506 binding protein (FKBP) multimerization domain polypeptide or variant thereof, and a CD4 transmembrane domain or an amnionless (AMN) transmembrane domain; wherein a bridging factor promotes the formation of a polypeptide complex on the non-natural cell surface with the bridging factor associated with and disposed between the multimerization domains of the first polypeptide and the second polypeptide and the multimerization domains of the first polypeptide and the third polypeptide.

In certain embodiments, the FKBP multimerization domain of the second polypeptide and/or the third polypeptide is FKBP12.

In further embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In various embodiments, the first polypeptide comprises a CD8α transmembrane domain; a CD137 co-stimulatory domain; and a CD3 ζ primary signaling domain.

In some embodiments, the second polypeptide and/or the third polypeptide comprises a CD4 transmembrane domain.

In certain embodiments, the binding domain of the second polypeptide and/or the third polypeptide comprises an antibody or antigen binding fragment thereof.

In various embodiments, the binding domain of the second polypeptide and/or the third polypeptide comprises an antibody or antigen binding fragment thereof selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In additional embodiments, the binding domain of the second polypeptide comprises an antibody or antigen binding fragment thereof that competes with the amino acid sequence set forth in SEQ ID NO: 2 or SEQ ID NO: 3, for binding to the amino acid set forth in SEQ ID NO: 1.

In some embodiments, the binding domain of the second polypeptide comprises the amino acid sequence set forth in SEQ ID NO: 2 or SEQ ID NO: 3.

In some embodiments, the binding domain of the third polypeptide binds a target antigen selected from the group consisting of: CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In some embodiments, the binding domain of the third polypeptide binds a target antigen selected from the group consisting of: CD123, CLL-1, MUC16, MICA, MICB, ULBP1, ULBP2, ULBP3, ULBP4, ULBP5, and ULBP6.

In various embodiments, the second polypeptide and/or the third polypeptide comprises a costimulatory domain.

In particular embodiments, the costimulatory domain of the second polypeptide and/or the third polypeptide is independently selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In certain embodiments, the costimulatory domain of the second polypeptide and/or the third polypeptide is independently selected from a costimulatory domain isolated from OX40 or TNFR2.

In some embodiments, the first polypeptide and/or the second polypeptide and/or the third polypeptide comprises a signal peptide.

In particular embodiments, the first polypeptide comprises a CD8α signal peptide.

In additional embodiments, the second polypeptide and/or the third polypeptide comprises an Igκ signal peptide.

In further embodiments, a non-natural cell comprises: a polypeptide complex that comprises a first polypeptide comprising an FRB multimerization domain polypeptide or variant thereof, a CD8α transmembrane domain or a CD4 transmembrane domain, a CD137 co-stimulatory domain, and/or a CD3 ζ primary signaling domain; a second polypeptide comprising a binding domain that binds to CD33, an FKBP multimerization domain polypeptide or variant thereof, and a CD4 transmembrane domain or a CD8α transmembrane domain; a third polypeptide comprising a binding domain comprising an scFv that binds a target antigen, an FKBP multimerization domain polypeptide or variant thereof, and a CD4 transmembrane domain or an amnionless (AMN) transmembrane domain; and a bridging factor associated with and disposed between the multimerization domains of the first and second polypeptides and the first and third polypeptides.

In various embodiments, the FKBP multimerization domain of the second polypeptide and/or the third polypeptide is FKBP12.

In particular embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a CD8α transmembrane domain; a CD137 co-stimulatory domain; and a CD3 ζ primary signaling domain.

In certain embodiments, the second polypeptide and/or the third polypeptide comprises a CD4 transmembrane domain.

In various embodiments, the binding domain of the second polypeptide and/or the third polypeptide comprises an antibody or antigen binding fragment thereof.

In some embodiments, the binding domain of the second polypeptide and/or the third polypeptide comprises an antibody or antigen binding fragment thereof selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In particular embodiments, the binding domain the second polypeptide and/or the third polypeptide comprises an antibody or antigen binding fragment thereof that competes with the amino acid sequence set forth in SEQ ID NO: 2 or SEQ ID NO: 3, for binding to the amino acid set forth in SEQ ID NO: 1.

In some embodiments, the binding domain of the second polypeptide comprises the amino acid sequence set forth in SEQ ID NO: 2 or SEQ ID NO: 3.

In some embodiments, the binding domain of the third polypeptide binds a target antigen selected from the group consisting of: CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In some embodiments, the binding domain of the third polypeptide binds a target antigen selected from the group consisting of: CD123, CLL-1, MUC16, MICA, MICB, ULBP1, ULBP2, ULBP3, ULBP4, ULBP5, and ULBP6.

In various embodiments, the second polypeptide and/or the third polypeptide comprises a costimulatory domain.

In additional embodiments, the costimulatory domain of the second polypeptide and/or the third polypeptide is independently selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In particular embodiments, the costimulatory domain of the second polypeptide and/or the third polypeptide is a costimulatory domain isolated from OX40 or TNFR2.

In some embodiments, the first polypeptide and/or the second polypeptide and/or the third polypeptide comprises a signal peptide.

In particular embodiments, the first polypeptide comprises a CD8α signal peptide.

In additional embodiments, the second polypeptide and/or the third polypeptide comprises an Igκ signal peptide.

In particular embodiments, the cell is a hematopoietic cell.

In certain embodiments, the cell is a T cell.

In various embodiments, the cell is a CD3+, CD4+, and/or CD8+ cell.

In some embodiments, the cell is an immune effector cell.

In further embodiments, the cell is a cytotoxic T lymphocytes (CTLs), a tumor infiltrating lymphocytes (TILs), or a helper T cell.

In various embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In additional embodiments, the FRB multimerization domain and the FKBP multimerization domain localize extracellularly when of the first polypeptide and the second polypeptide are expressed.

In certain embodiments, a fusion polypeptide comprises: a first polypeptide comprising an FRB multimerization domain polypeptide or variant thereof, a CD8α transmembrane domain or a CD4 transmembrane domain, a CD137 co-stimulatory domain, and/or a CD3 ζ primary signaling domain; a polypeptide cleavage signal; a second polypeptide comprising a binding domain that binds to CD33, an FKBP multimerization domain polypeptide or variant thereof, and a CD4 transmembrane domain or a CD8α transmembrane domain; a second polypeptide cleavage signal; and a third polypeptide comprising a binding domain that binds to a target antigen, an FKBP multimerization domain polypeptide or variant thereof, and a CD4 transmembrane domain or an amnionless (AMN) transmembrane domain.

In various embodiments, the FKBP multimerization domain of the second polypeptide and/or the third polypeptide is FKBP12.

In some embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In some embodiments, the first polypeptide comprises a CD8α transmembrane domain; a CD137 co-stimulatory domain; and a CD3 ζ primary signaling domain.

In certain embodiments, the second polypeptide and/or the third polypeptide comprises a CD4 transmembrane domain.

In various embodiments, the binding domain of the second polypeptide and/or the third polypeptide comprises an antibody or antigen binding fragment thereof.

In additional embodiments, the binding domain of the second polypeptide and/or the third polypeptide comprises an antibody or antigen binding fragment thereof is selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In particular embodiments, the binding domain of the second polypeptide comprises an antibody or antigen binding fragment thereof that competes with the amino acid sequence set forth in SEQ ID NO: 2 or SEQ ID NO: 3, for binding to the amino acid set forth in SEQ ID NO: 1.

In some embodiments, the binding domain of the second polypeptide comprises the amino acid sequence set forth in SEQ ID NO: 2 or SEQ ID NO: 3.

In some embodiments, the binding domain of the third polypeptide binds a target antigen selected from the group consisting of: CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In some embodiments, the binding domain of the third polypeptide binds a target antigen selected from the group consisting of: CD123, CLL-1, MUC16, MICA, MICB, ULBP1, ULBP2, ULBP3, ULBP4, ULBP5, and ULBP6.

In various embodiments, the second polypeptide and/or the third polypeptide comprises a costimulatory domain.

In some embodiments, the costimulatory domain of the second polypeptide and/or the third polypeptide is independently selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In particular embodiments, the costimulatory domain of the second polypeptide and/or the third polypeptide is independently selected from a costimulatory domain isolated from OX40 or TNFR2.

In certain embodiments, the first polypeptide cleavage signal and/or the second polypeptide cleavage signal is a viral self-cleaving polypeptide.

In various embodiments, the first polypeptide cleavage signal and/or the second polypeptide cleavage signal is a viral self-cleaving 2A polypeptide.

In additional embodiments, the first polypeptide cleavage signal and/or the second polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In some embodiments, the FRB multimerization domain and the FKBP multimerization domain localize extracellularly when of the first polypeptide and the second polypeptide and/or the third polypeptide are expressed.

In some embodiments, the first polypeptide and/or the second polypeptide and/or the third polypeptide comprises a signal peptide.

In particular embodiments, the first polypeptide comprises a CD8α signal peptide.

In additional embodiments, the second polypeptide and/or the third polypeptide comprises an Igκ signal peptide.

In various embodiments, a polypeptide complex comprises: a first polypeptide comprising an FRB multimerization domain polypeptide or variant thereof, a CD8α transmembrane domain or a CD4 transmembrane domain, a CD137 co-stimulatory domain, and/or a CD3 ζ primary signaling domain; a second polypeptide comprising a binding domain that binds to CD33, an FKBP multimerization domain polypeptide or variant thereof, and a CD4 transmembrane domain or a CD8α transmembrane domain; a third polypeptide comprising a binding domain that binds a target antigen, an FKBP multimerization domain polypeptide or variant thereof, and a CD4 transmembrane domain or an amnionless (AMN) transmembrane domain; and a bridging factor associated with and disposed between the multimerization domains of the first polypeptide and the second polypeptide and the first polypeptide and the third polypeptide, when the first polypeptide and the second polypeptide and the third polypeptide are expressed in a cell.

In some embodiments, the FKBP multimerization domain of the second polypeptide and/or the third polypeptide is FKBP12.

In certain embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a CD8α transmembrane domain; a CD137 co-stimulatory domain; and a CD3 ζ primary signaling domain.

In various embodiments, the second polypeptide and/or the third polypeptide comprises a CD4 transmembrane domain.

In particular embodiments, the binding domain of the second polypeptide and/or the third polypeptide comprises an antibody or antigen binding fragment thereof.

In some embodiments, the binding domain of the second polypeptide and/or the third polypeptide comprises an antibody or antigen binding fragment thereof selected from the group consisting of: a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In various embodiments, the binding domain of the second polypeptide comprises an antibody or antigen binding fragment thereof that competes with the amino acid sequence set forth in SEQ ID NO: 2 or SEQ ID NO: 3, for binding to the amino acid set forth in SEQ ID NO: 1.

In some embodiments, the binding domain of the second polypeptide comprises the amino acid sequence set forth in SEQ ID NO: 2 or SEQ ID NO: 3.

In some embodiments, the binding domain of the third polypeptide binds a target antigen selected from the group consisting of: CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

In some embodiments, the binding domain of the third polypeptide binds a target antigen selected from the group consisting of: CD123, CLL-1, MUC16, MICA, MICB, ULBP1, ULBP2, ULBP3, ULBP4, ULBP5, and ULBP6.

In various embodiments, the second polypeptide and/or the third polypeptide comprises a costimulatory domain.

In some embodiments, the costimulatory domain of the second polypeptide and/or the third polypeptide is independently selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In various embodiments, the costimulatory domain of the second polypeptide and/or the third polypeptide is independently selected from a costimulatory domain isolated from OX40 or TNFR2.

In some embodiments, the first polypeptide and/or the second polypeptide and/or the third polypeptide comprises a signal peptide.

In particular embodiments, the first polypeptide comprises a CD8α signal peptide.

In additional embodiments, the second polypeptide and/or the third polypeptide comprises an Igκ signal peptide.

In additional embodiments, the cell is a hematopoietic cell.

In particular embodiments, the cell is a T cell.

In further embodiments, the cell is a CD3+, CD4+, and/or CD8+ cell.

In some embodiments, the cell is an immune effector cell.

In certain embodiments, the cell is a cytotoxic T lymphocytes (CTLs), a tumor infiltrating lymphocytes (TILs), or a helper T cell.

In various embodiments, the cell is a natural killer (NK) cell or natural killer T (NKT) cell.

In additional embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the FRB multimerization domain and the FKBP multimerization domain localize extracellularly when of the first polypeptide and the second polypeptide and/or the third polypeptide are expressed.

In some embodiments, a polynucleotide encodes a first polypeptide, a second polypeptide, a third polypeptide or a fusion polypeptide contemplated herein.

In particular embodiments, the polynucleotide encoding the first polypeptide and/or the second polypeptide and/or the third polypeptide and/or the fusion polypeptide comprises a post-transcriptional regulatory element.

In certain embodiments, the polynucleotide encoding the fusion polypeptide comprises a post-transcriptional regulatory element.

In further embodiments, the post-transcriptional regulatory element is a woodchuck hepatitis virus posttranscriptional regulatory element (WPRE) or a hepatitis B virus posttranscriptional regulatory element (HPRE).

In additional embodiments, a cDNA encodes a first polypeptide, a second polypeptide, a third polypeptide or a fusion polypeptide contemplated herein.

In various embodiments, an RNA encodes a first polypeptide, a second polypeptide, a third polypeptide or a fusion polypeptide contemplated herein.

In certain embodiments, a vector comprises a polynucleotide contemplated herein.

In particular embodiments, the vector is an expression vector.

In particular embodiments, the vector is a transposon.

In additional embodiments, the vector is a piggyBAC transposon or a Sleeping Beauty transposon.

In some embodiments, the vector is a viral vector.

In various embodiments, the vector is an adenoviral vector, an adeno-associated viral (AAV) vector, a herpes virus vector, a vaccinia virus vector, or a retroviral vector.

In some embodiments, the retroviral vector is a lentiviral vector.

In certain embodiments, the lentiviral vector is selected from the group consisting of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In various embodiments, a composition comprising a non-natural cell, a fusion polypeptide, a polynucleotide, or a vector contemplated herein.

In particular embodiments, a pharmaceutical composition comprises a pharmaceutically acceptable carrier and a non-natural cell, a fusion polypeptide, a polynucleotide, or a vector contemplated herein.

In additional embodiments, method of treating a subject in need thereof comprising administering the subject an effective amount of a composition contemplated herein.

In particular embodiments, a method of treating, preventing, or ameliorating at least one symptom of a cancer, infectious disease, autoimmune disease, inflammatory disease, and immunodeficiency, or condition associated therewith, comprises administering to the subject an effective amount of a composition contemplated herein.

In some embodiments, a method of treating a solid cancer comprises administering to the subject an effective amount of a composition contemplated herein.

In various embodiments, the solid cancer is selected from the group consisting of: lung cancer, liver cancer, gastric cancer, colorectal cancer, head and neck cancer, urothelial cancer, prostate cancer, testicular cancer, endometrial cancer, pancreatic cancer, breast cancer, cervical cancer, ovarian cancer, skin cancer, and melanoma.

In certain embodiments, a method of treating a hematological malignancy comprises administering to the subject an effective amount of a composition contemplated herein.

In various embodiments, the hematological malignancy is a leukemia, lymphoma, or multiple myeloma.

In particular embodiments, the hematological malignancy is acute myelogenous leukemia (AML).

BRIEF DESCRIPTION OF THE SEQUENCE IDENTIFIERS

Figure 1:
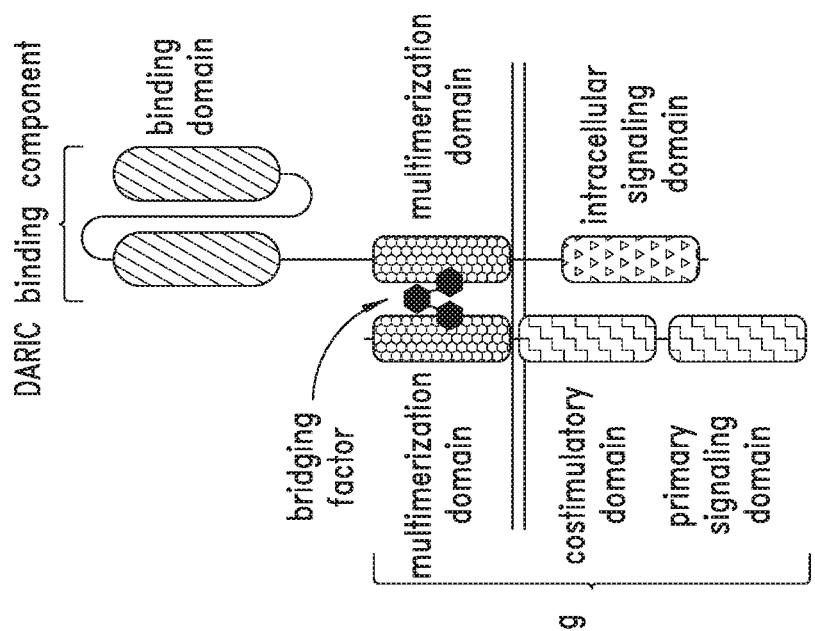
FIG. 1 shows a cartoon of representative CD33 DARICs.
Figure 1:
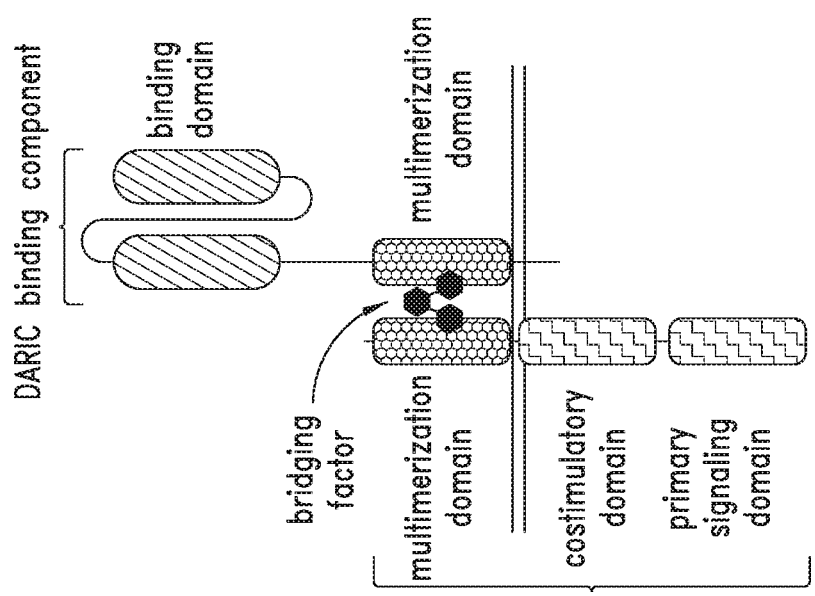

SEQ ID NO: 1 sets forth the amino acid sequence for human CD33.

SEQ ID NO: 2 sets forth the amino acid sequence for an anti-CD33 scFv.

SEQ ID NO: 3 sets forth the amino acid sequence for an anti-CD33 scFv.

SEQ ID NO: 4 sets forth the amino acid sequence for a CD33 DARIC fusion protein.

SEQ ID NO: 5 sets forth the amino acid sequence for a CD33 DARIC fusion protein.

SEQ ID NO: 6 sets forth the amino acid sequence for a CD33 DARIC fusion protein comprising a CD33.OX40 DARIC binding component.

SEQ ID NO: 7 sets forth the amino acid sequence for a CD33 DARIC fusion protein comprising a CD33.OX40 DARIC binding component.

SEQ ID NO: 8 sets forth the amino acid sequence for a CD33 DARIC fusion protein comprising a CD33.TNFR2 DARIC binding component.

SEQ ID NO: 9 sets forth the amino acid sequence for a CD33 DARIC fusion protein comprising a CD33.TNFR2 DARIC binding component.

SEQ ID NOs: 10-20 set forth the amino acid sequences of various linkers.

SEQ ID NOs: 21-45 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

Cancer is among the leading causes of death worldwide. About 10% of cancers are hematological malignancies, which includes leukemia, lymphomas, and myelomas. In 2012, the worldwide incidence of acute myelogenous leukemia (AML) was about 351,965 and about 265, 461 people died from AML.

CD33 is expressed on the majority of acute myeloid leukemia (AML) leukemic blasts and, possibly, leukemic stem cells. CD33 is a challenging target because of its low expression and slow internalization; these characteristics limit antibody-dependent cell-mediated cytotoxicity and intracellular drug accumulation and, consequently, the activity of unlabeled and toxin-carrying antibodies.

One promising strategy to target cancers expressing CD33 is adoptive cellular immunotherapy using immune effector cells genetically engineered to express chimeric antigen receptors (CAR) that bind CD33 or a dual targeting DARIC that binds cells expressing CD33 and another antigen expressed on the target cells, e.g., CD123, CLL-1. However, a significant limitation of CAR T cell therapy is the lack of spatial and temporal control of the CAR T cell activity. Lack of control over CAR T cell activity can trigger a range of side effects, many of which begin subtly but can rapidly worsen. A particularly severe complication is cytokine release syndrome (CRS) or "cytokine storm" where CAR T cells induce massive and potentially fatal cytokine release. CRS can produce dangerously high fevers, extreme fatigue, difficulty breathing, and a sharp drop in blood pressure. CRS can also produce a second wave of side effects that involve the nervous system, including neurotoxicity, tremors, headaches, confusion, loss of balance, trouble speaking, seizures, and hallucinations. The compositions and methods contemplated herein offer solutions to these and other problems plaguing adoptive cell therapies.

The disclosure generally relates to improved compositions and methods for regulating the spatial and temporal control of adoptive cell therapies using dimerizing agent regulated immunoreceptor complexes (DARICs) that bind CD33. Without wishing to be bound by any particular theory, DARIC compositions and methods contemplated herein provide numerous advantages over CAR T cell therapies existing in the art, including but not limited to, both spatial and temporal control over immune effector cell signal transduction binding and signaling activities. DARIC temporal control primes the DARIC machinery for signaling through bridging factor mediated association of a DARIC binding component to a DARIC signaling component. DARIC spatial control engages the signaling machinery through recognition of CD33 by the DARIC binding domain of the DARIC binding component. In this manner, DARIC immune effector cells become activated when both a target cell expressing CD33 and a bridging factor are present. In addition, dual targeting of target cells expressing CD33 and another target antigen may be advantageous in enhancing efficacy, tumor clearance, and safety; and in decreasing relapse, antigen escape, on-target off-tumor cell lysis.

In various embodiments, the disclosure contemplates CD33 DARIC components that generate an anti-cancer response against cancers that express CD33, e.g., AML.

In particular embodiments, a DARIC includes a polypeptide (DARIC signaling component) that comprises a multimerization domain polypeptide or variant thereof, a transmembrane domain, a costimulatory domain; and/or a primary signaling domain; and a polypeptide (DARIC binding component) that comprises a binding domain that CD33, a multimerization domain polypeptide or variant thereof, a transmembrane domain; and optionally a costimulatory domain. In the presence of a bridging factor, the DARIC binding and signaling components associate with one another through the bridging factor to form a functionally active DARIC.

In various embodiments, the disclosure contemplates DARIC components that generate an anti-cancer response against cancers that express CD33 and another antigen expressed on one or more target cells.

In particular embodiments, a DARIC includes a polypeptide (DARIC signaling component) that comprises a multimerization domain polypeptide or variant thereof, a transmembrane domain, a costimulatory domain; and/or a primary signaling domain; a polypeptide (DARIC binding component) that comprises a binding domain that binds CD33, a multimerization domain polypeptide or variant thereof, a transmembrane domain; and optionally a costimulatory domain; and polypeptide (DARIC binding component) that comprises a binding domain that binds another target antigen, e.g., CD123, CLL-1, a multimerization domain polypeptide or variant thereof, a transmembrane domain. In the presence of a bridging factor, the DARIC binding components each associate with the DARIC signaling component through the bridging factor to form functionally active DARICs.

In preferred embodiments, the multimerization domains of the DARIC binding and DARIC signaling components are positioned extracellularly. Extracellular position of the multimerization domains provides numerous advantages over intracellular positioning including, but not limited to, more efficient positioning of the binding domain, higher temporal sensitivity to bridging factor regulation, and less toxicity due to ability to use non-immunosuppressive doses of particular bridging factors.

Polynucleotides encoding DARICs, DARIC binding components, and DARIC signaling components; DARIC binding components, DARIC signaling components, DARIC protein complexes, DARIC fusion proteins; cells comprising polynucleotides encoding DARICs, DARIC binding components, and DARIC signaling components and/or expressing the same; and methods of using the same to treat an immune disorder are contemplated herein.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology,* Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir andCC Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" refers to a portion of CD33, that a binding domain contemplated herein, is designed to bind. In particular embodiments, the target antigen is an epitope of the amino acid sequence set forth in SEQ ID NO: 1. In other embodiments, the target antigen is an antigen expressed on target cell, a cancer cell, e.g., CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1). In one embodiment, the antigen is an MHC-peptide complex, such as a class I MHC-peptide complex or a class II MHC-peptide complex.

"CD33" refers to a cell surface receptor also known as sialic-acid-binding immunoglobulin-like lectin 3 (SIGLEC-3) or GP67. The CD33 gene is located on chromosome 19 and produces a glycosylated protein of about 67 kD. CD33 has two Ig-like domains, one V-set domain and one C2-set domain. CD33 plays a role in mediating cell-cell interactions and in maintaining immune cells in a resting state. CD33 recognizes and binds alpha-2,3- and more avidly alpha-2,6-linked sialic acid-bearing glycans. Upon engagement of ligands such as C1q or sialylated glycoproteins, two immunoreceptor tyrosine-based inhibitory motifs (ITIMs) located in CD33 cytoplasmic tail are phosphorylated by Src-like kinases such as LCK. These phosphorylations provide docking sites for the recruitment and activation of protein-tyrosine phosphatases PTPN6/SHP-1 and PTPN11/SHP-2. CD33 is normally expressed on subsets of normal B cells and activated T cells and natural killer cells but is not expressed on hematopoietic stem cells or outside the hematopoietic system. CD33 is also expressed in acute myeloid leukemia (AML) blast cells in a majority of AML patients.

As used herein, the terms, "binding domain," "extracellular domain," "antigen binding domain," "extracellular binding domain," "extracellular antigen binding domain," "antigen-specific binding domain," and "extracellular antigen specific binding domain," are used interchangeably and provide a polypeptide with the ability to specifically bind to the target antigen of interest. The binding domain may be derived either from a natural, synthetic, semi-synthetic, or recombinant source.

The terms "specific binding affinity" or "specifically binds" or "specifically bound" or "specific binding" or "specifically targets" as used herein, describe binding of binding domain to a target antigen at greater binding affinity than background binding. A binding domain "specifically binds" to a target antigen, if it binds to or associates with the antigen with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein comprising the same) binds to a target with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains (or single chain fusion proteins thereof) refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

The terms "selectively binds" or "selectively bound" or "selectively binding" or "selectively targets" and describe preferential binding of one molecule to a target molecule (on-target binding) in the presence of a plurality of off-target molecules.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

An "epitope" or "antigenic determinant" refers to the region of an antigen to which a binding agent binds. In a preferred embodiment, the epitope is an amino acid sequence of a CD33 polypeptide. In another embodiment, the epitope is a portion of a polypeptide selected from the group consisting of: CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, and WT-1. In particular embodiments, the polypeptide is intracellular and the epitope is a short oligopeptide (about 2 to about 20 amino acids) displayed in complex with an MHC.

Antibodies include antigen binding fragments thereof, such as a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

A "linker" refers to a plurality of amino acid residues between the various polypeptide domains added for appropriate spacing and conformation of the molecule. In particular embodiments, the linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions. In particular embodiments, a linker separates one or more heavy or light chain variable domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 10); TGEKP (SEQ ID NO: 11) (see, e.g., Liu et al., PNAS 5525-5530 (1997)); GGRR (SEQ ID NO: 12) (Pomerantz et al. 1995, supra); (GGGGS)$_n$ wherein n=1, 2, 3, 4 or 5 (SEQ ID NO: 13) (Kim et al., PNAS 93, 1156-1160 (1996); EGKSSGSGSESKVD (SEQ ID NO: 14) (Chaudhary et al., 1990, Proc. Natl. Acad. Sci. U.S.A.

87:1066-1070); KESGSVSSEQLAQFRSLD (SEQ ID NO: 15) (Bird et al., 1988, Science 242:423-426), GGRRGGGS (SEQ ID NO: 16) LRQRDGERP (SEQ ID NO: 17); LRQKDGGGSERP (SEQ ID NO: 18); LRQKD(GGGS)$_2$ERP (SEQ ID NO: 19). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 20) (Cooper et al., *Blood*, 101 (4): 1637-1644 (2003)).

A "spacer domain," refers to a polypeptide that separates two domains. In one embodiment, a spacer domain moves an antigen binding domain away from the effector cell surface to enable proper cell/cell contact, antigen binding and activation (Patel et al., *Gene Therapy*, 1999; 6:412-419). In particular embodiments, a spacer domain separates one or more heavy or light chain variable domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

A "multimerization domain," as used herein, refers to a polypeptide that preferentially interacts or associates with another different polypeptide directly or via a bridging molecule, e.g., a chemically inducible dimerizer, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FK506 binding protein (FKBP) polypeptide or variants thereof, an FKBP-rapamycin binding (FRB) polypeptide or variants thereof, a calcineurin polypeptide or variants thereof, a cyclophilin polypeptide or variants thereof, a bacterial dihydrofolate reductase (DHFR) polypeptide or variants thereof, a PYR1-like 1 (PYL1) polypeptide or variants thereof, an abscisic acid insensitive 1 (ABI1) polypeptide or variants thereof, a GIB1 polypeptide or variants thereof, or a GAI polypeptide or variants thereof.

As used herein, the term "FKBP-rapamycin binding polypeptide" refers to an FRB polypeptide. In particular embodiments, the FRB polypeptide is an FKBP12-rapamycin binding polypeptide. FRB polypeptides suitable for use in particular embodiments contemplated herein generally contain at least about 85 to about 100 amino acid residues. In certain embodiments, the FRB polypeptide comprises a 93 amino acid sequence Ile-2021 through Lys-2113 and a mutation of T2098L, with reference to GenBank Accession No. L34075.1. An FRB polypeptide contemplated herein binds to an FKBP polypeptide through a bridging factor, thereby forming a ternary complex.

As used herein, the term "FK506 binding protein" refers to an FKBP polypeptide. In particular embodiments, the FKBP polypeptide is an FKBP12 polypeptide or an FKBP12 polypeptide comprising an F36V mutation. In certain embodiments, an FKBP domain may also be referred to as a "rapamycin binding domain". Information concerning the nucleotide sequences, cloning, and other aspects of various FKBP species is known in the art (see, e.g., Staendart et al., *Nature* 346:671, 1990 (human FKBP12); Kay, *Biochem. J.* 314:361, 1996). An FKBP polypeptide contemplated herein binds to an FRB polypeptide through a bridging factor, thereby forming a ternary complex.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to AP21967, rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include, but are not limited to, those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 (also known as C-16-(S)-7-methylindolerapamycin, IC$_{50}$=10 nM, a chemically modified non-immunosuppressive rapamycin analogue). Other illustrative rapalogs suitable for use in particular embodiments contemplated herein include, but are not limited to, everolimus, novolimus, pimecrolimus, ridaforolimus, tacrolimus, temsirolimus, umirolimus, and zotarolimus.

A "substantially reduced immunosuppressive effect" refers to at least less than 0.1 to 0.005 times the immunosuppressive effect observed or expected for the same dose measured either clinically or in an appropriate in vitro (e.g., inhibition of T cell proliferation) or in vivo surrogate of human immunosuppressive activity.

A "transmembrane domain" or "TM domain" is a domain that anchors a polypeptide to the plasma membrane of a cell. The TM domain may be derived either from a natural, synthetic, semi-synthetic, or recombinant source.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

An "intracellular signaling domain" or "endodomain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces an effector function signal. The term intracellular signaling domain is meant to include any truncated portion of an intracellular signaling domain necessary or sufficient to transduce an effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to an intracellular signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70).

An "immune disorder" refers to a disease that evokes a response from the immune system. In particular embodiments, the term "immune disorder" refers to a cancer, an autoimmune disease, or an immunodeficiency.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a neglible amount of antigen that is undetectable. In one embodiment, antigen negative cells do not bind receptors directed to the antigen. In one embodiment, antigen negative cells do not substantially bind receptors directed to the antigen.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response.

Additional definitions are set forth throughout this disclosure.

C. CD33 DARICS

In particular embodiments, one or more DARIC receptors that redirect cytotoxicity of immune effector cells toward cancer cells expressing CD33 are contemplated. As used herein, the term "CD33 DARIC receptor" refers to one or more non-naturally occurring polypeptides that transduces an immunostimulatory signal in an immune effector cell upon exposure to antigen and a multimerizing agent or bridging factor, e.g., stimulating immune effector cell activity and function, increasing production and/or secretion of proinflammatory cytokines. In preferred embodiments, a CD33 DARIC is a multi-chain chimeric receptor comprising one or more DARIC signaling components and one or more DARIC binding components that recognize CD33.

In particular embodiments, a CD33 DARIC signaling component, a CD33 binding component, and another DARIC binding component that is directed against another target antigen, e.g., CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1 are contemplated.

In one embodiment, a DARIC signaling component and a DARIC binding component are expressed from the same cell. In another embodiment, a DARIC signaling component and one or more DARIC binding components are expressed from different cells. In a particular embodiment, a DARIC signaling component is expressed from a cell and one or more DARIC binding components are supplied exogenously, as a polypeptide. In one embodiment, one or more DARIC binding components pre-loaded with a bridging factor is supplied exogenously to a cell expressing a DARIC signaling component.

1. CD33 DARIC Signaling Component

A "DARIC signaling component" or "DARIC signaling polypeptide" refers to a polypeptide comprising one or more multimerization domains, a transmembrane domain, and one or more intracellular signaling domains. In particular embodiments, a DARIC signaling component comprises a multimerization domain, a transmembrane domain, a costimulatory domain and/or a primary signaling domain. In particular embodiments, a DARIC signaling component comprises a first multimerization domain, a first transmembrane domain, a first costimulatory domain and/or a primary signaling domain.

In particular embodiments, a DARIC signaling component comprises one or more multimerization domains.

Illustrative examples of multimerization domains suitable for use in particular CD33 DARIC signaling components contemplated herein include, but are not limited to, an FK506 binding protein (FKBP) polypeptide or variants thereof, an FKBP-rapamycin binding (FRB) polypeptide or variants thereof, a calcineurin polypeptide or variants thereof, a cyclophilin polypeptide or variants thereof, a bacterial dihydrofolate reductase (DHFR) polypeptide or variants thereof, a PYR1-like 1 (PYL1) polypeptide or variants thereof and an abscisic acid insensitive 1 (ABI1) polypeptide or variants thereof.

In particular embodiments, a CD33 DARIC signaling component comprises an FRB polypeptide. In a preferred embodiment, a CD33 DARIC signaling component comprises an FRB polypeptide comprising a T2098L mutation, or variant thereof.

In particular preferred embodiments, a CD33 DARIC signaling component comprises an FRB polypeptide comprising a T2098L mutation, or variant thereof. In certain preferred embodiments, a CD33 DARIC signaling component comprises an FKBP12 polypeptide or variant thereof.

In particular embodiments, a DARIC signaling component comprises a transmembrane domain.

Illustrative examples of transmembrane domains suitable for use in particular CD33 DARIC signaling components contemplated herein include, but are not limited to, the transmembrane region(s) of the alpha, beta, gamma, or delta chain of a T-cell receptor, CD3ε, CD3ζ, CD4, CD5, CD8a, CD9, CD 16, CD22, CD27, CD28, CD33, CD37, CD45, CD64, CD71, CD80, CD86, CD 134, CD137, CD152, CD 154, amnionless (AMN), and programmed cell death 1 (PDCD1). In a preferred embodiment, a CD33 DARIC signaling component comprises a CD4 transmembrane domain. In a preferred embodiment, a CD33 DARIC signaling component comprises a CD8α transmembrane domain.

In particular embodiments, a DARIC signaling component comprises a linker that links the C-terminus of the transmembrane domain to the N-terminus of an intracellular signaling domain. In various preferred embodiments, a short oligo- or poly-peptide linker, preferably between 1, 2, 3, 4, 5, 6, 7, 8, 9, or 10 amino acids in length links the transmembrane domain and an intracellular signaling domain. A glycine-serine based linker provides a particularly suitable linker.

DARIC signaling components contemplated in particular embodiments herein comprise one or more intracellular signaling domains. In one embodiment, a CD33 DARIC signaling component comprises one or more costimulatory signaling domains and/or a primary signaling domain. In one embodiment, the intracellular signaling domain comprises an immunoreceptor tyrosine activation motif (ITAM).

Illustrative examples of ITAM containing primary signaling domains that are suitable for use in particular CD33 DARIC signaling components contemplated herein include, but are not limited to those derived from FcRγ, FcRβ, CD3γ, CD3δ, CD3ε, CD3ζ, CD22, CD79a, CD79b, and CD66d. In preferred embodiments, a CD33 DARIC signaling component comprises a CD32 primary signaling domain and one or more costimulatory signaling domains. The primary signaling and costimulatory signaling domains may be linked in any order in tandem to the carboxyl terminus of the transmembrane domain.

Illustrative examples of costimulatory domains suitable for use in particular CD33 DARIC signaling components contemplated herein include, but are not limited to those domains isolated from the following costimulatory molecules: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70).

In particular embodiments, a CD33 DARIC signaling component contemplated herein comprises a signal peptide, e.g., secretion signal peptide, and do not comprise a transmembrane domain. Illustrative examples of signal peptides suitable for use in particular CD33 DARIC signaling components include but are not limited to an IgG1 heavy chain signal polypeptide, an Igκ light chain signal polypeptide, a CD8α signal polypeptide, or a human GM-CSF receptor alpha signal polypeptide. In various preferred embodiments, a CD33 DARIC signaling component comprises a CD8α signal polypeptide.

In particular embodiments, a CD33 DARIC signaling component comprises one or more costimulatory signaling domains selected from the group consisting of CD28, CD137, and CD134. In particular embodiments, a CD33 DARIC signaling component comprises one or more costimulatory signaling domains selected from the group consisting of CD28, CD137, and CD134, and a CD3 ζ primary signaling domain. In a particular embodiment, a CD33 DARIC signaling component comprises a CD137 costimulatory domain and a CD3ζ primary signaling domain.

In a preferred embodiment, a CD33 DARIC signaling component comprises an FRB T2098L multimerization domain, a CD8α transmembrane domain, a CD137 costimulatory domain and a CD3ζ primary signaling domain.

2. CD33 DARIC Binding Component

A "DARIC binding component" or "DARIC binding polypeptide" refers to a polypeptide comprising a binding domain that binds one or more CD33 epitopes and one or more multimerization domains. In particular embodiments, the DARIC binding component comprises a binding domain that binds one or more CD33 epitopes, a second multimerization domain, and a second transmembrane domain. In particular embodiments, the DARIC binding component comprises a multimerization domain and a transmembrane domain, e.g., a second transmembrane domain. In other particular embodiments, the DARIC binding component comprises a multimerization domain, a transmembrane domain and one or more intracellular signaling domains. In particular embodiments, the DARIC binding component comprises a binding domain that binds one or more CD33 epitopes, a second multimerization domain, a second transmembrane domain, and a second costimulatory domain.

Illustrative examples of binding domains suitable for use in particular DARIC binding components include, but are not limited to, antibodies or antigen binding fragments thereof, that bind to one or more CD33 epitopes, and/or amino acids of SEQ ID NO: 1.

In particular embodiments, one or more DARIC binding components comprises are expressed: a DARIC binding component that comprises a binding domain that binds CD33, a second multimerization domain, a second transmembrane domain, and optionally, a second costimulatory domain; and a DARIC binding component that comprises a binding domain that binds an antigen expressed on a target cell.

Illustrative examples of binding domains suitable for use in particular DARIC binding components include, but are not limited to, antibodies or antigen binding fragments thereof, that bind to one or more epitopes of: CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1.

Illustrative examples of antibodies and antigen binding fragments thereof suitable for use in particular DARIC binding components include, but are not limited to, a Camel Ig, a Llama Ig, an Alpaca Ig, Ig NAR, a Fab' fragment, a F(ab')2 fragment, a bispecific Fab dimer (Fab2), a trispecific Fab trimer (Fab3), an Fv, an single chain Fv protein ("scFv"), a bis-scFv, (scFv)2, a minibody, a diabody, a triabody, a tetrabody, a disulfide stabilized Fv protein ("dsFv"), and a single-domain antibody (sdAb, a camelid VHH, Nanobody).

In particular embodiments, antibodies and antigen binding fragments thereof suitable for use in particular DARIC binding components include, but are not limited to, murine antibodies, camelid antibodies, chimeric antibodies, humanized antibodies, or human antibodies. In particular embodiments, the antibody or antigen binding fragment thereof is derived from a monoclonal antibody.

In particular embodiments, the binding domain comprises one or more humanized camelid VHH antibodies that bind to one or more CD33 epitopes, and/or amino acids of SEQ ID NO: 1.

In particular preferred embodiments, the binding domain is a humanized or human scFv that binds to one or more CD33 epitopes, and/or amino acids of SEQ ID NO: 1.

In certain preferred embodiments, the binding domain is a humanized or human scFv that competes with an antibody or antigen binding fragment thereof comprising the amino acid sequence set forth in SEQ ID NO: 2 or 3 for binding to one or more CD33 epitopes, and/or amino acids of SEQ ID NO: 1.

In other preferred embodiments, the binding domain is an scFv comprising the amino acid sequence set forth in SEQ ID NO: 2 or 3.

In particular embodiments, the binding domain comprises one or more humanized camelid VHH antibodies that bind to CD33 and one or more scFvs or humanized camelid VHH antibodies that bind a target antigen expressed on a target cell.

In particular preferred embodiments, the binding domain is a humanized or human scFv that binds to CD33.

In particular embodiments, the binding domain comprises one or more scFvs that bind to CD33 and one or more humanized camelid VHH antibodies or scFvs that bind an antigen expressed on a target cell.

In particular embodiments, a DARIC binding component comprises one or more multimerization domains.

Illustrative examples of multimerization domains suitable for use in particular DARIC binding components contemplated herein include, but are not limited to, an FKBP polypeptide or variants thereof, an FRB polypeptide or variants thereof, a calcineurin polypeptide or variants thereof, a cyclophilin polypeptide or variants thereof, a DHFR polypeptide or variants thereof, a PYL1 polypeptide or variants thereof and an ABI1 polypeptide or variants thereof.

In particular embodiments, a DARIC binding component comprises an FRB polypeptide or variant thereof and a DARIC signaling component comprises an FKBP polypeptide or variant thereof. In a preferred embodiment, a DARIC binding component comprises an FRB polypeptide comprising a T2098L mutation, or variant thereof and a DARIC signaling component comprises an FKBP12 polypeptide or variant thereof.

In particular embodiments, a DARIC binding component comprises an FKBP polypeptide or variant thereof and a DARIC signaling component comprises an FRB polypeptide, or variant thereof. In a preferred embodiment, a DARIC binding component comprises an FKBP12 polypeptide, or variant thereof and a DARIC signaling component comprises an FRB polypeptide comprising a T2098L mutation, or variant thereof.

In particular embodiments, a DARIC binding component comprises a transmembrane domain. In one embodiment, the transmembrane domain may be the same as the transmembrane domain used in the DARIC signaling component. In one embodiment, the transmembrane domain may be different from the transmembrane domain used in the DARIC signaling component.

Illustrative examples of transmembrane domains suitable for use in particular DARIC binding components contemplated herein include, but are not limited to, the transmembrane region(s) of the alpha, beta, gamma, or delta chain of a T-cell receptor, CD3ε, CD3ζ, CD4, CD5, CD8a, CD9, CD 16, CD22, CD27, CD28, CD33, CD37, CD45, CD64, CD71, CD80, CD86, CD 134, CD137, CD152, CD 154, amnionless (AMN), and programmed cell death 1 (PDCD1). In a preferred embodiment, a CD33 DARIC binding component comprises a CD8α transmembrane domain. In a preferred embodiment, a CD33 DARIC binding component comprises a CD4 transmembrane domain.

In various preferred embodiments, a short oligo- or polypeptide linker, preferably between 1, 2, 3, 4, 5, 6, 7, 8, 9, or 10 amino acids in length links the transmembrane domain and the intracellular signaling domain. A glycine-serine based linker provides a particularly suitable linker.

DARIC binding components contemplated in particular embodiments herein do not comprise one or more intracellular signaling domains.

In other particular embodiments, DARIC binding components contemplated herein comprise one or more intracellular signaling domains. In preferred embodiments, wherein the DARIC binding component comprises one or more intracellular signaling domains, those domains are different that the intracellular signaling domains present in the cognate DARIC signaling component. In one embodiment, a DARIC binding component comprises a costimulatory signaling domain.

Illustrative examples of costimulatory domains suitable for use in particular DARIC signaling components contemplated herein include, but are not limited to those domains isolated from the following costimulatory molecules: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70).

In particular embodiments, a DARIC binding component contemplated herein comprises a signal peptide, e.g., secretion signal peptide, and do not comprise a transmembrane domain. Illustrative examples of signal peptides suitable for use in particular DARIC binding components include but are not limited to an IgG1 heavy chain signal polypeptide, an Igκ light chain signal polypeptide, a CD8α signal polypeptide, or a human GM-CSF receptor alpha signal polypeptide. In various preferred embodiments, a DARIC binding component comprises a CD8α signal polypeptide.

In particular embodiments, a CD33 DARIC binding component comprises an scFv that binds to CD33, an FKBP12 multimerization domain, and a CD4 transmembrane domain and optionally, a costimulatory domain.

In certain embodiments, a CD33 DARIC binding component comprises an scFv that binds to CD33, and an FKBP12 multimerization domain.

In some embodiments, a CD33 DARIC binding component comprises an scFv that competes with an antibody or antigen binding fragment thereof comprising the amino acid sequence set forth in SEQ ID NO: 2 or 3 for binding to CD33, an FKBP12 multimerization domain, and a CD4 transmembrane domain and optionally, a costimulatory domain.

In particular embodiments, a CD33 DARIC binding component comprises an scFv that competes with an antibody or antigen binding fragment thereof comprising the amino acid sequence set forth in SEQ ID NO: 2 or 3 for binding to CD33, and an FKBP12 multimerization domain.

In some embodiments, a CD33 DARIC binding component comprises the amino acid sequence set forth in SEQ ID NO: 2 or 3, an FKBP12 multimerization domain, and a CD4 transmembrane domain and optionally, a costimulatory domain.

In particular embodiments, a CD33 DARIC binding component comprises the amino acid sequence set forth in SEQ ID NO: 2 or 3, and an FKBP12 multimerization domain.

In particular embodiments, a DARIC binding component comprises a binding domain that binds an antigen expressed on a target cell, e.g., CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1, an FKBP12 multimerization domain, and a CD4 transmembrane domain or an AMN transmembrane domain, and optionally a TNFR2 costimulatory domain.

In particular embodiments, a DARIC binding component comprises a binding domain that binds a target antigen selected from the group consisting of: CD123, CLL-1, MICA, MICB, ULBP1, ULBP2, ULBP3, ULBP4, ULBP5, and ULBP6, an FKBP12 multimerization domain, and a CD4 transmembrane domain or an AMN transmembrane domain, and optionally a TNFR2 costimulatory domain.

3. Bridging Factor

Bridging factors contemplated in particular embodiments herein, mediate or promote the association of one or more DARIC signaling components with one or more DARIC binding components through multimerization domains in the respective components. A bridging factor associates with and is disposed between the multimerization domains to promote association of a DARIC signaling component and a DARIC binding component. In the presence of a bridging factor, the DARIC binding component and the DARIC signaling component associate and initiate immune effector cell activity against a target cell when the DARIC binding polypeptide is bound to a target antigen on the target cell. In the absence of a bridging factor, the DARIC binding component does not associate with the DARIC signaling component and the DARIC is inactive.

In particular embodiments, a CD33 DARIC signaling component and a CD33 DARIC binding component comprise a cognate pair of multimerization domains selected from the group consisting of: FKBP and FKBP12-rapamycin binding (FRB), FKBP and calcineurin, FKBP and cyclophilin, FKBP and bacterial dihydrofolate reductase (DHFR), calcineurin and cyclophilin, and PYR1-like 1 (PYL1) and abscisic acid insensitive 1 (ABI1).

In certain embodiments, the multimerization domains of DARIC signaling and binding components associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, and trimethoprim (Tmp)-synthetic ligand for FK506 binding protein (FKBP) (SLF) or a derivative thereof.

In particular embodiments, a CD33 DARIC signaling component and a CD33 DARIC binding component comprise one or more FRB and/or FKBP multimerization domains or variants thereof. In certain embodiments, a CD33 DARIC signaling component comprises an FRB multimerization domain or variant thereof and a CD33 DARIC binding component comprises an FKBP multimerization domain or variant thereof. In particular preferred embodiments, a CD33 DARIC signaling component comprises an FRB T2098L multimerization domain or variant thereof and a CD33 DARIC binding component comprises an FKBP12 or FKBP12 F36V multimerization domains or variant thereof.

In particular embodiments, a CD33 DARIC signaling component, a CD33 DARIC binding component, and a DARIC binding component that binds a target antigen expressed on a target cell comprise one or more FRB and/or FKBP multimerization domains or variants thereof. In certain embodiments, a CD33 DARIC signaling component comprises an FRB multimerization domain or variant thereof and a CD33 DARIC binding component and a DARIC binding component that binds another target antigen comprise an FKBP multimerization domain or variant thereof. In particular preferred embodiments, a CD33 DARIC signaling component comprises an FRB T2098L multimerization domain or variant thereof and a CD33 DARIC binding component and a DARIC binding component that binds a target cell antigen comprise an FKBP12 or FKBP12 F36V multimerization domains or variant thereof.

Illustrative examples of bridging factors suitable for use in particular embodiments contemplated herein include, but are not limited to, AP1903, AP20187, AP21967 (also known as C-16-(S)-7-methylindolerapamycin), everolimus, novolimus, pimecrolimus, ridaforolimus, tacrolimus, temsirolimus, umirolimus, and zotarolimus. In particular preferred embodiments, the bridging factor is AP21967. In certain preferred embodiments, the bridging factor is a non-immunosuppressive dose of sirolimus (rapamycin).

D. Engineered Antigen Receptors

In particular embodiments, a cell is engineered or modified to express a CD33 DARIC and an engineered antigen receptor. In particular embodiments, a nucleic acid or vector encodes a fusion polypeptide comprising an engineered receptor and a CD33 DARIC binding component and/or a CD33 DARIC signaling component, and one or more polypeptide cleavage signals interspersed between the receptor and the components. In other particular embodiments, a polynucleotide or vector encoding a CD33 DARIC is introduced into an immune effector cell that comprises an engineered antigen receptor. Without wishing to be bound by any particular theory, it is contemplated in particular embodiments, that any mechanism known in the art may be used to introduce and co-express an engineered antigen receptor and a CD33 DARIC in the same immune effector cell or population of cells to the efficiency, potency, and durability of the immune effector cell response. In particular embodiments, the intracellular signaling domains, e.g., costimulatory domains, of the engineered antigen receptor and the CD33 DARIC signaling domains and/or the CD33 DARIC binding will be different from each other.

In particular embodiments, immune effector cells contemplated herein comprise an engineered antigen receptor and one or more components of a CD33 DARIC. In particular embodiments, the engineered antigen receptor is an engineered T cell receptor (TCR), a chimeric antigen receptor (CAR), or a zetakine.

1. Engineered TCRs

In particular embodiments, immune effector cells contemplated herein comprise an engineered TCR and a CD33 DARIC. In one embodiment, T cells are engineered by introducing a polynucleotide or vector encoding an engineered TCR and one or more components of a CD33 DARIC separated by one or more polypeptide cleavage signals. In one embodiment, T cells are engineered by introducing a polynucleotide or vector encoding an engineered TCR and a polynucleotide or vector encoding one or more components of a CD33 DARIC. In one embodiment, T cells are engineered to express an engineered TCR are further engineered by introducing a polynucleotide or vector encoding one or more components of a CD33 DARIC.

Naturally occurring T cell receptors comprise two subunits, an alpha chain and a beta chain subunit ($\alpha\beta$TCR), or a gamma chain and a delta chain subunit ($\gamma\delta$TCR), each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy. In one embodiment, the TCR is an $\alpha\beta$TCR. In one embodiment, the TCR is a $\gamma\delta$TCR.

In one embodiment, T cells are modified by introducing a TCR subunit that has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. In particular embodiments, the essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the alpha chain or beta chain of a TCR, or of the gamma chain or delta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor (FR$\alpha$), $\alpha_v\beta_6$ integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-10R$\alpha$, IL-13R$\alpha$2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA 10, melanoma antigen recognized by T cells 1 (MelanA or MART1), Mesothelin (MSLN), MUC1, MUC16, MHC class I chain related proteins A (MICA), MHC class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

2. Chimeric Antigen Receptors

In particular embodiments, immune effector cells contemplated herein comprise a CAR and a CD33 DARIC. Chimeric antigen receptors (CARs) are molecules that combine antibody-based specificity for a target antigen (e.g., tumor antigen) with a T cell receptor-activating intracellular domain to generate a chimeric protein that exhibits a specific antitumor cellular immune activity. As used herein, the term, "chimeric," describes being composed of parts of different proteins or DNAs from different origins.

In one embodiment, T cells are engineered by introducing a polynucleotide or vector encoding a CAR and one or more CD33 DARIC components separated by one or more polypeptide cleavage signals. In one embodiment, T cells are engineered by introducing a polynucleotide or vector encoding a CAR and a polynucleotide or vector encoding one or more CD33 DARIC components. In one embodiment, T cells that are engineered to express a CAR are further engineered by introducing a polynucleotide or vector encoding one or more CD33 DARIC components.

In various embodiments, a CAR comprises an extracellular domain that binds to a specific target antigen (also referred to as a binding domain or antigen-specific binding domain), a transmembrane domain and one or more intracellular signaling domains. The main characteristic of CARs is their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide. In preferred embodiments, a CAR binds a target polypeptide that is different than the target polypeptide(s) bound by a DARIC binding component, i.e., the CAR does not bind CD33. A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

In one preferred embodiment, the binding domain comprises an scFv.

In another preferred embodiment, the binding domain comprises one or more camelid antibodies.

In particular embodiments, a CAR comprises an extracellular domain that binds an antigen selected from the group consisting of: FRα, $α_vβ_6$ integrin, BCMA, B7-H3, B7-H6, CAIX, CD16, CD19, CD20, CD22, CD30, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-10Rα, IL-13Rα2, Kappa, LAGE-1A, Lambda, LeY, L1-CAM, MAGE-A1, MAGE-A3, MAGE-A4, MAGE-A6, MAGE-A10, MART1, MSLN, MUC1, MUC16, MICA, MICB, NCAM, NY-ESO-1, PLAC1, PRAME, PSCA, PSMA, ROR1, SSX2, Survivin, TAG72, TEM1, TEM7R, TPBG, ULBP 1, ULBP2, ULBP3, ULBP4, ULBP5, ULBP6, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In one embodiment, the spacer domain comprises the CH2 and CH3 of IgG1, IgG4, or IgD.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region.

In one embodiment, the hinge is a PD-1 hinge or CD152 hinge.

The transmembrane (TM) domain of the CAR fuses the extracellular binding portion and intracellular signaling domain and anchors the CAR to the plasma membrane of the immune effector cell. The TM domain may be derived either from a natural, synthetic, semi-synthetic, or recombinant source.

Illustrative™ domains may be derived from (i.e., comprise at least the transmembrane region(s) of the alpha, beta, gamma, or delta chain of a T-cell receptor, CD3ε, CD3ζ, CD4, CD5, CD8α, CD9, CD 16, CD22, CD27, CD28, CD33, CD37, CD45, CD64, CD71, CD80, CD86, CD 134, CD137, CD152, CD 154, AMN, and PDCD1.

In one embodiment, a CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In preferred embodiments, a CAR comprises an intracellular signaling domain that comprises one or more costimulatory signaling domains and a primary signaling domain.

Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors.

Illustrative examples of such costimulatory molecules suitable for use in CARs contemplated in particular embodiments include, but are not limited to, TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD94, CD134 (OX40), CD137 (4-1BB), CD278 (ICOS), DAP10, LAT, SLP76, TRAT1, TNFR2, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

In various embodiments, the CAR comprises: an extracellular domain that binds an antigen selected from the group consisting of: BCMA, B7-H3, CD19, CD20, CD22, CD79A, CD79B, EGFR, EGFRvIII, and an NKG2D ligand; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

3. Zetakines

In various embodiments, immune effector cells contemplated herein comprise one or more chains of a zetakine receptor and a CD33 DARIC. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In one embodiment, T cells are engineered by introducing a polynucleotide or vector encoding one or more chains of a zetakine receptor and one or more CD33 DARIC components separated by one or more polypeptide cleavage signals. In one embodiment, T cells are engineered by introducing a polynucleotide or vector encoding one or more chains of a zetakine receptor and a polynucleotide or vector encoding one or more CD33 DARIC components. In one embodiment, T cells are engineered to express one or more chains of a zetakine receptor are further engineered by introducing a polynucleotide or vector encoding one or more CD33 DARIC components.

In particular embodiments, the zetakine comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha, beta, gamma, or delta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD94, CD134 (OX40), CD137 (4-1BB), CD278 (ICOS), DAP10, LAT, SLP76, TRAT1, TNFR2, and ZAP70.

In one embodiment, a chimeric cytokine receptor comprises one or more costimulatory signaling domains selected from the group consisting of CD28, CD137, and CD134, and a CD3 ζ primary signaling domain.

E. Polypeptides

Various polypeptides are contemplated herein, including, but not limited to, CD33 DARICs, CD33 DARIC binding components, CD33 DARIC signaling components, DARIC binding components that bind antigens expressed on a target cell, engineered TCRs, CARs, zetakines, fusion proteins comprising the foregoing polypeptides and fragments thereof. In preferred embodiments, a polypeptide comprises an amino acid sequence set forth in any one of SEQ ID NOs: 1-9. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring. In particular preferred embodiments, fusion polypeptides, polypeptides, fragments and other variants thereof are prepared, obtained, or isolated from one or more human polypeptides.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence. In particular embodiments, the biological activity is binding affinity. In particular embodiments, the biological activity is enzymatic activity.

In certain embodiments, a CD33 DARIC comprises a polypeptide complex comprising (i) a first polypeptide, e.g., first fusion polypeptide, having a first multimerization domain and (ii) second polypeptide, e.g., second fusion polypeptide, having a second multimerization domain.

In certain embodiments, a CD33 DARIC comprises a polypeptide complex comprising (i) a first polypeptide, e.g., first fusion polypeptide, comprising a first multimerization domain (ii) a second polypeptide, e.g., second fusion polypeptide, comprising a second multimerization domain; and (iii) a third polypeptide, e.g., third fusion polypeptide, comprising a third multimerization domain.

In particular embodiments, the multimerization domains are the same; in certain embodiments, the first multimerization domain is different than the second and/or third multimerization domains. In particular embodiments, the second and third multimerization domains are the same. In particular embodiments, the second and third multimerization domains are different. The first and second multimerization domains and/or the first and third multimerization domains substantially contribute to or efficiently promote formation of the polypeptide complex in the presence of a bridging factor. The interaction(s) between the first and second multimerization domains and/or the first and third multimerization domains substantially contributes to or efficiently promotes the multimerization of the first and second fusion polypeptides and/or first and third fusion polypeptides if there is a statistically significant reduction in the association between the first and second fusion polypeptides and/or the first and third fusion polypeptides in the absence of the first multimerization domain, the second multimerization domain, or the bridging factor. In certain embodiments, when the first and second (and/or third) fusion polypeptides are co-expressed, at least about 60%, for instance, at least about 60% to about 70%, at least about 70% to about 80%, at least about 80% to about 90%, 91%, 92%, 93%, 94%, 95%, 96%, 97%, 98%, 99%, or 100%, and at least about 90% to about 92%, 93%, 94%, 95%, 96%, 97%, 98%, or 99% of the first and second (and/or third) single chain polypeptides form multimers with each other in the presence of a bridging factor.

Polypeptides variants include biologically active "polypeptide fragments." Illustrative examples of biologically active polypeptide fragments include binding domains, intracellular signaling domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X." "X" if present in an amino acid SEQ ID NO, refers to any one or more amino acids. In particular embodiments, SEQ ID NOs denoting a fusion protein comprise a sequence of continuous X residues that cumulatively represent any amino acid sequence.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82:488-492), Kunkel et al., (1987, *Methods in Enzymol,* 154:367-382), U.S. Pat. No. 4,873,192, Watson, J. D. et al., (*Molecular Biology of the Gene,* Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed. Res. Found.,* Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

| Amino Acid Codons | | | | | | | |
|---|---|---|---|---|---|---|---|
| Amino Acids | One letter code | Three letter code | Codons | | | | |
| Alanine | A | Ala | GCA | GCC | GCG | | GCU |
| Cysteine | C | Cys | UGC | | | UGU | |
| Aspartic acid | D | Asp | GAC | | | GAU | |
| Glutamic acid | E | Glu | GAA | | | GAG | |
| Phenylalanine | F | Phe | UUC | | | UUU | |
| Glycine | G | Gly | GGA | GGC | GGG | | GGU |
| Histidine | H | His | CAC | | | CAU | |
| Isoleucine | I | Iso | AUA | AUC | | AUU | |
| Lysine | K | Lys | AAA | | | AAG | |
| Leucine | L | Leu | UUA | UUG | CUA | CUC | CUG | CUU |
| Methionine | M | Met | | | AUG | | |
| Asparagine | N | Asn | AAC | | | AAU | |
| Proline | P | Pro | CCA | CCC | CCG | | CGU |
| Glutamine | Q | Gln | CAA | | | CAG | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU |
| Valine | V | Val | GUA | GUC | GUG | | GUU |
| Tryptophan | W | Trp | | | UGG | | |
| Tyrosine | Y | Tyr | UAC | | | UAU | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p.224).

In one embodiment, where expression of two or more polypeptides is desired, the polynucleotide sequences encoding them can be separated by an IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments. In preferred embodiments, a fusion polypeptide comprises one or more CD33 DARIC components. In other preferred embodiments, the fusion polypeptide comprises one or more CD33 DARICs.

In another embodiment, two or more CD33 DARIC components and/or other polypeptides can be expressed as a fusion protein that comprises one or more self-cleaving peptide sequences between the polypeptides as disclosed elsewhere herein.

In particular embodiments, a fusion polypeptide comprises a CD33 DARIC signaling component, a CD33 binding component, and another DARIC binding component that is directed against another target antigen.

In particular embodiments, a fusion polypeptide comprises a CD33 DARIC signaling component, a CD33 binding component, and another DARIC binding component that is directed against another target antigen, e.g., CD7, CD13, CD15, CD30, CD38, CD44v6, CD45, CD47, CD70, CD123, C-type lectin-like molecule-1 (CLL-1), fms related tyrosine kinase 3 (FLT3), Lambda, Lewis-Y (LeY), MHC class I chain related proteins A (MICA), MHC class I chain related proteins B (MICB), T-cell immunoglobulin and mucin domain-containing molecule 3 (TIM3), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

Fusion polypeptides can comprise one or more polypeptide domains or segments including, but not limited to signal peptides, cell permeable peptide domains (CPP), binding domains, signaling domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise one or more linkers that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. In particular embodiments, preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains nonessential N-terminal amino acid regions that can be used to separate the functional domains and prevent steric interference. In particular embodiments, preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5 (8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ (G/S) (SEQ ID NO: 21), for example, ENLYFQG (SEQ ID NO: 22) and ENLYFQS (SEQ ID NO: 23), wherein X represents any amino acid (cleavage by TEV occurs between Q and G or Q and S).

In particular embodiments, the polypeptide cleavage signal is a viral self-cleaving peptide or ribosomal skipping sequence.

Illustrative examples of ribosomal skipping sequences include, but are not limited to: a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

| SEQ ID NO: 24 | GSGATNFSLLKQAGDVEENPGP |
| --- | --- |
| SEQ ID NO: 25 | ATNFSLLKQAGDVEENPGP |
| SEQ ID NO: 26 | LLKQAGDVEENPGP |
| SEQ ID NO: 27 | GSGEGRGSLLTCGDVEENPGP |
| SEQ ID NO: 28 | EGRGSLLTCGDVEENPGP |
| SEQ ID NO: 29 | LLTCGDVEENPGP |
| SEQ ID NO: 30 | GSGQCTNYALLKLAGDVESNPGP |
| SEQ ID NO: 31 | QCTNYALLKLAGDVESNPGP |
| SEQ ID NO: 32 | LLKLAGDVESNPGP |
| SEQ ID NO: 33 | GSGVKQTLNFDLLKLAGDVESNPGP |
| SEQ ID NO: 34 | VKQTLNFDLLKLAGDVESNPGP |
| SEQ ID NO: 35 | LLKLAGDVESNPGP |
| SEQ ID NO: 36 | LLNFDLLKLAGDVESNPGP |
| SEQ ID NO: 37 | TLNFDLLKLAGDVESNPGP |
| SEQ ID NO: 38 | LLKLAGDVESNPGP |
| SEQ ID NO: 39 | NFDLLKLAGDVESNPGP |
| SEQ ID NO: 40 | QLLNFDLLKLAGDVESNPGP |
| SEQ ID NO: 41 | APVKQTLNFDLLKLAGDVESNPGP |
| SEQ ID NO: 42 | VTELLYRMKRAETYCPRPLLAIHPTEARHKQKIVAPVKQT |
| SEQ ID NO: 43 | LNFDLLKLAGDVESNPGP |
| SEQ ID NO: 44 | LLAIHPTEARHKQKIVAPVKQTLNFDLLKLAGDVESNPGP |
| SEQ ID NO: 45 | EARHKQKIVAPVKQTLNFDLLKLAGDVESNPGP |

In preferred embodiments, a polypeptide or fusion polypeptide comprises one or more CD33 DARIC components or CD33 DARICs. In preferred embodiments, a fusion polypeptide comprises one or more CD33 DARIC components or CD33 DARICs separated by one or more self-cleaving polypeptides.

In particular embodiments, a fusion polypeptide comprises a CD33 DARIC signaling component comprising an FRB T2098L multimerization domain, a CD8α transmembrane domain, a CD137 costimulatory domain and a CD3 ζ primary signaling domain; a viral self-cleaving 2A polypeptide; and a CD33 DARIC binding component comprising an antibody or antigen binding fragment thereof, that binds to CD33, an FKBP12 multimerization domain polypeptide, and a CD4 transmembrane domain.

In particular embodiments, a fusion polypeptide comprises a CD33 DARIC signaling component comprising an FRB T2098L multimerization domain, a CD8α transmembrane domain, a CD137 costimulatory domain and a CD3ζ primary signaling domain; a viral self-cleaving 2A polypeptide; and a CD33 DARIC binding component comprising an antibody or antigen binding fragment thereof, that binds to CD33, a CD4 transmembrane domain, and optionally a CD27, CD28, TNFRS14, TNFRS18, TNFRS25, OX40 or TNFR2 costimulatory domain.

In particular embodiments, a polypeptide or fusion polypeptide comprises a CD33 DARIC signaling component, a CD33 DARIC binding component comprising an antibody or antigen binding fragment thereof; and a DARIC binding component that binds another target antigen. In preferred embodiments, a fusion polypeptide comprises a CD33 DARIC signaling component, a CD33 DARIC binding component and a DARIC binding component separated by one or more self-cleaving polypeptides.

In particular embodiments, a fusion polypeptide comprises a CD33 DARIC signaling component comprising an FRB T2098L multimerization domain, a CD8α transmembrane domain, a CD137 costimulatory domain and a CD3ζ primary signaling domain; a first viral self-cleaving 2A polypeptide; a CD33 DARIC binding component comprising an scFv that binds to CD33, an FKBP12 multimerization domain polypeptide, and a CD4 transmembrane domain or an AMN transmembrane domain; a second viral self-cleaving 2A polypeptide; a DARIC binding component comprising an scFv that binds a target antigen selected from the group consisting of: CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, and WT-1, an FKBP12 multimerization domain polypeptide, and a CD4 transmembrane domain or an AMN transmembrane domain.

In particular embodiments, a fusion polypeptide comprises a CD33 DARIC signaling component comprising an FRB T2098L multimerization domain, a CD8α transmembrane domain, a CD137 costimulatory domain and a CD3 ζ primary signaling domain; a first viral self-cleaving 2A polypeptide; a CD33 DARIC binding component comprising an scFv that binds to CD33, an FKBP12 multimerization domain polypeptide, and a CD4 transmembrane domain or an AMN transmembrane domain, and optionally a CD27, CD28, TNFRS14, TNFRS18, TNFRS25, OX40 or TNFR2 costimulatory domain; a second viral self-cleaving 2A polypeptide; a DARIC binding component comprising an scFv that a target antigen selected from the group consisting of: CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, and WT-1, and a CD4 transmembrane domain or an AMN transmembrane domain, and optionally a CD27, CD28, TNFRS14, TNFRS18, TNFRS25, OX40 or TNFR2 costimulatory domain.

In particular embodiments, a fusion polypeptide comprises a CD33 DARIC signaling component comprising an FRB T2098L multimerization domain, a CD8α transmembrane domain, a CD137 costimulatory domain and a CD3ζ primary signaling domain; a viral self-cleaving 2A polypeptide; a CD33 DARIC binding component comprising an scFv that binds to CD33, an FKBP12 multimerization domain polypeptide, and a CD4 transmembrane domain or an AMN transmembrane domain, and optionally a CD27, CD28, TNFRS14, TNFRS18, TNFRS25, OX40 or TNFR2 costimulatory domain; and a DARIC binding component comprising a binding domain that binds CD123, CLL-1, MICA, MICB, ULBP1, ULBP2, ULBP3, ULBP4, ULBP5, or ULBP6, a CD4 transmembrane domain, and optionally a CD27, CD28, TNFRS14, TNFRS18, TNFRS25, OX40 or TNFR2 costimulatory domain; wherein the DARIC components are separated from each other by a viral self-cleaving 2A polypeptide.

F. Polynucleotides

In particular embodiments, polynucleotides encoding a CD33 DARIC, one or more DARIC components, engineered TCRs, CARs, zetakines, fusion proteins comprising the foregoing polypeptides and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

As used herein, "isolated polynucleotide" refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" also refers to a complementary DNA (cDNA), a recombinant DNA, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein. In certain embodiments, the mRNA comprises a cap, one or more nucleotides, and a poly(A) tail.

In particular embodiments, polynucleotides encoding one or more DARIC components may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose.

Illustrative examples of polynucleotides include, but are not limited to, polynucleotides encoding polypeptides set forth in SEQ ID NOs: 1-9.

In various illustrative embodiments, polynucleotides contemplated herein include, but are not limited to polynucleotides encoding one or more CD33 DARIC components, CD33 DARIC receptors, DARIC binding components that a target antigen, engineered antigen receptors, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to, pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector including an origin of replication, selection cassettes, promoters, enhancers, translation initiation signals (Shine Dalgarno sequence or Kozak sequence) introns, a polyadenylation sequence, 5' and 3' untranslated regions, all of which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoML V) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) U3 promoter (Haas et al. *Journal of Virology.* 2003; 77 (17): 9439-9450).

In one embodiment, a vector comprises an MNDU3 promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc. Inducer agents include, but are not limited to glucocorticoids, estrogens, mifepristone (RU486), metals, interferons, small molecules, cumate, tetracycline, doxycycline, and variants thereof.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15 (12): 477-83) and Jackson and Kaminski. 1995. RNA 1 (10): 985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18 (11): 6178-6190), the fibroblast growth factor 2 (FGF-2), and insulin-like growth factor (IGFII), the translational initiation factor eIF4G and yeast transcription factors TFIID and HAP4, the encephelomyocarditis virus (EMCV) which is commercially available from Novagen (Duke et al., 1992. J. Virol 66 (3): 1602-9) and the VEGF IRES (Huez et al., 1998. Mol Cell Biol 18 (11): 6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides a consensus Kozak sequence. As used herein, the term "Kozak sequence" refers to a short nucleotide sequence that greatly facilitates the initial binding of mRNA to the small subunit of the ribosome and increases translation. The consensus Kozak sequence is (GCC) RCCATGG (SEQ ID NO: 46), where R is a purine (A or G) (Kozak, 1986. *Cell.* 44 (2): 283-92, and Kozak, 1987. *Nucleic Acids Res.* 15 (20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a poly A tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal poly A sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art. In particular embodiments, the poly(A) sequence is synthetic.

In particular embodiments, polynucleotides encoding one or more polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid: nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising polynucleotides contemplated herein are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include, but are not limited to, adeno-associated virus (AAV), retrovirus, herpes simplex virus, adenovirus, and vaccinia virus vectors.

In various embodiments, one or more polynucleotides encoding one or more CD33 DARIC components and/or other DARIC binding components and/or other polypeptides contemplated herein are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype.

For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding one or more CD33 DARIC components and/or other DARIC binding components and/or other polypeptides contemplated herein are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to, HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Y) packaging signal, an export element, poly(A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65:1053; and Cullen et al., 1991. *Cell* 58:423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from −418 to −18), without significant reductions in vector titers.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4" presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4 (4): 495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding one or more CD33 DARIC components and/or other DARIC binding components and/or other polypeptides contemplated herein are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding one or more CD33 DARIC components and/or other DARIC binding components and/or other polypeptides contemplated herein are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genetically Modified Cells

In various embodiments, cells are modified to express one or more CD33 DARICs, CD33 DARIC components, and/or other DARIC binding components, engineered TCRs, CARs, zetakines, and/or fusion proteins contemplated herein, for use in the treatment of cancer. Cells may be non-genetically modified to express one or more of the polypeptides contemplated herein, or in particular preferred embodiments, cells may be genetically modified to express one or more of the polypeptides contemplated herein. In particular embodiments, engineered TCR-expressing or CAR T cells are modified to express a CD33 DARIC signaling component, a CD33 DARIC binding component, and a DARIC binding component that binds another target antigen. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

In particular embodiments, one or more CD33 DARIC components contemplated herein are introduced and expressed in immune effector cells to improve the efficacy of the immune effector cells. In particular embodiments, one or more CD33 DARIC components are introduced and expressed in immune effector cells that have been redirected to a target cell by virtue of co-expressing an engineered antigen receptor in the cell.

In particular embodiments, a dual targeting immune effector cell is contemplated where the target cell expresses CD33, recognized by a CD33 DARIC.

In particular embodiments, a dual targeting immune effector cell is contemplated where the target cell expresses CD33 recognized by a CD33 DARIC receptor and an antigen recognized by another DARIC binding component. It particular embodiments, the other DARIC binding component binds CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, including but not limited to cytotoxic T cells (CTLs; $CD8^+$ T cells), TILs, and helper T cells (HTLs; $CD4^+$ T cells. In a particular embodiment, the cells comprise αβ T cells. In a particular embodiment, the cells comprise γδ T cells. In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are human autologous immune effector cells.

Illustrative immune effector cells suitable for introducing one or more CD33 DARIC components or a CD33 DARIC contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), $CD4^+CD8^+$ T cell, $CD4^-CD8^-$ T cell, or any other subset of T cells. Other illustrative populations of T cells suitable for use in particular embodiments include naïve T cells and memory T cells.

As would be understood by the skilled person, other cells may also be used as immune effector cells comprising one or more CD33 DARIC components or a CD33 DARIC contemplated herein. In particular embodiments, immune effector cells also include NK cells, NKT cells, neutrophils, and macrophages. Immune effector cells also include progenitors of effector cells wherein such progenitor cells can be induced to differentiate into immune effector cells in vivo or in vitro. Thus, in particular embodiments, immune effector cells include progenitors of immune effectors cells such as hematopoietic stem cells (HSCs) contained within the $CD34^+$ population of cells derived from cord blood, bone marrow or mobilized peripheral blood which upon administration in a subject differentiate into mature immune effector cells, or which can be induced in vitro to differentiate into mature immune effector cells.

The term, "$CD34^+$ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The $CD34^+$ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express one or more CD33 DARIC components, and optionally another DARIC binding component contemplated herein are provided in particular embodiments. In one embodiment, the method comprises transfecting or transducing immune effector cells isolated from an individual such that the immune effector cells with one or more nucleic acids and/or vectors or combination thereof comprising one or more CD33 DARIC components, optionally in combination with another DARIC binding component, contemplated herein. In one embodiment, the method comprises transfecting or transducing immune effector cells isolated from an individual such that the immune effector cells express one or more CD33 DARIC components and engineered antigen receptors contemplated herein. In one embodiment, the method comprises transfecting or transducing immune effector cells isolated from an individual such that the immune effector cells express one or more CD33 DARIC components and a DARIC binding component that binds another target antigen, e.g., CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1.

In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a $CD3^+$, $CD4^+$, $CD8^+$, or a combination thereof.

In certain embodiments, the T cells are isolated from an individual and first activated and stimulated to proliferate in vitro prior to being modified to express one or more CD33 DARIC components.

In order to achieve sufficient therapeutic doses of T cell compositions, T cells are often subjected to one or more rounds of stimulation, activation and/or expansion. In particular embodiments, T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding one or more CD33 DARIC components, optionally in combination with an engineered antigen receptor contemplated herein.

In one embodiment, T cells are activated at the same time that they are modified.

In various embodiments, a method of generating an immune effector cell comprises activating a population of cells comprising T cells and expanding the population of T cells. T cell activation can be accomplished by providing a primary stimulation signal through the T cell TCR/CD3 complex and by providing a secondary co-stimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, co-stimulatory signal. In particular embodiments, a CD28 binding agent can be used to provide a co-stimulatory signal. Illustrative examples of CD28 binding agents include but are not limited to: natural CD 28 ligands, e.g., a natural ligand for CD28 (e.g., a member of the B7 family of proteins, such as B7-1 (CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the co-stimulatory molecule are coupled to the same surface.

In certain embodiments, binding agents that provide stimulatory and co-stimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the co-stimulatory molecule are displayed on antigen presenting cells.

In one embodiment, the molecule providing the primary stimulation signal, for example a molecule which provides stimulation through the TCR/CD3 complex and the co-stimulatory molecule are provided on separate surfaces.

In a certain embodiment, one of the binding agents that provides stimulatory and co-stimulatory signals is soluble (provided in solution) and the other agent(s) is provided on one or more surfaces.

In a particular embodiment, the binding agents that provide stimulatory and co-stimulatory signals are both provided in a soluble form (provided in solution).

In various embodiments, the methods for making T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02).

In particular embodiments, PBMCs or isolated T cells are contacted with a stimulatory agent and co-stimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and CIR cells to direct the stable expression and secretion, of a variety of co-stimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of co-stimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In a particular embodiment, a polynucleotide encoding one or more CD33 DARIC components is introduced into the population of T cells. In a particular embodiment, a polynucleotide encoding one or more CD33 DARIC components is introduced into a population of T cells that express an engineered antigen receptor. The polynucleotides may be introduced into the T cells by microinjection, transfection, lipofection, heat-shock, electroporation, transduction, gene gun, microinjection, DEAE-dextran-mediated transfer, and the like.

In a particular embodiment, a polynucleotide encoding one or more CD33 DARIC components and a DARIC binding component that binds a target antigen expressed on a target cell is introduced into the population of T cells.

In a preferred embodiment, polynucleotides are introduced into a T cell by viral transduction.

Illustrative examples of viral vector systems suitable for introducing a polynucleotide into an immune effector cell or CD34+ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

H. Compositions and Formulations

The compositions contemplated herein may comprise a CD33 DARIC, a CD33 DARIC and an engineered antigen receptor, or a CD33 DARIC signaling component, a CD33 DARIC binding component and a DARIC binding component that binds another target antigen, polynucleotides encoding the polypeptides, vectors comprising same, genetically modified immune effector cells comprising the polynucleotides or vectors and expressing the polypeptides, bridging factors, etc. Compositions include, but are not limited to, pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the bridging factors, polypeptides, polynucleotides, vectors comprising same, or genetically modified immune effector cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the bridging factors, polypeptides, polynucleotides, vectors comprising same, or genetically modified immune effector cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

In particular embodiments, compositions contemplated herein comprise a bridging factor and a pharmaceutically acceptable carrier.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the modified T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of modified T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better-defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to, QBSF-60 (Quality Biological, Inc.), StemPro-34 (Life Technologies), and X-VIVO 10.

In one embodiment, the compositions comprising modified T cells are formulated in PlasmaLyte.

In various embodiments, compositions comprising modified T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, PA: Pharmaceutical Press; 2012, which is incorporated by reference herein, in its entirety.

In particular embodiments, compositions comprise an amount of immune effector cells that express one or more CD33 DARIC components contemplated herein. In particular embodiments, compositions comprise an amount of immune effector cells that express an engineered antigen receptor and one or more CD33 DARIC components contemplated herein. In particular embodiments, compositions comprise an amount of immune effector cells that express a CD33 DARIC signaling component, a CD33 DARIC binding component, and a DARIC binding component that binds a target antigen contemplated herein. As used herein, the term "amount" refers to "an amount effective" or "an effective amount" of cells comprising one or more CD33 DARIC components contemplated herein, etc., to achieve a beneficial or desired prophylactic or therapeutic result in the presence of a bridging factor, including clinical results.

A "prophylactically effective amount" refers to an amount of cells comprising one or more CD33 DARIC components contemplated herein, etc., effective to achieve the desired prophylactic result in the presence of a bridging factor. Typically but not necessarily, since a prophylactic dose is used in subjects prior to or at an earlier stage of disease, the prophylactically effective amount is less than the therapeutically effective amount.

A "therapeutically effective amount" refers to an amount of cells comprising one or more CD33 DARIC components contemplated herein that is effective to "treat" a subject (e.g., a patient) in the presence of a bridging factor. When a therapeutic amount is indicated, the precise amount of the compositions to be administered, cells, bridging factor, etc, can be determined by a physician with consideration of individual differences in age, weight, tumor size, extent of infection or metastasis, and condition of the patient (subject).

It can generally be stated that a pharmaceutical composition comprising the immune effector cells described herein may be administered at a dosage of 102 to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered.

If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, the immune effector cells may be administered either alone, or as a pharmaceutical composition in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In particular embodiments, pharmaceutical compositions comprise an amount of bridging factor, in combination with one or more pharmaceutically or physiologically acceptable carriers, diluents or excipients.

In a particular embodiment, compositions comprise an effective amount of immune effector cells a CD33 DARIC signaling component and a CD33 DARIC binding component, and optionally a DARIC binding component that binds a target antigen contemplated herein, alone or in combination with a bridging factor and/or one or more therapeutic agents, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In a particular embodiment, a composition comprising an effective amount of immune effector cells comprising a CD33 DARIC signaling component and a CD33 DARIC binding component, and optionally a DARIC binding component that binds a target antigen contemplated herein is administered to a subject, and a composition comprising an effective amount of a bridging factor is administered to the subject, before, during, in combination with or subsequently to the cellular composition, and optionally repetitively administered to the subject.

In certain embodiments, compositions comprising immune effector cells comprising a CD33 DARIC signaling component and a CD33 DARIC binding component, and optionally a DARIC binding component that binds a target antigen contemplated herein may be administered in conjunction with any number of chemotherapeutic agents.

A variety of other therapeutic agents may be used in conjunction with the compositions described herein. In one embodiment, the composition comprising immune effector cells comprising a CD33 DARIC signaling component and a CD33 DARIC binding component, and optionally a DARIC binding component that binds a target antigen contemplated herein is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), non-steroidal anti-inflammatory drugs (NSAIDS) including aspirin, ibuprofen, naproxen, methotrexate, sulfasalazine, leflunomide, anti-TNF medications, cyclophosphamide and mycophenolate.

Illustrative examples of therapeutic antibodies suitable for combination treatment with the modified T cells comprising a CD33 DARIC signaling component and a CD33 DARIC binding component, and optionally a DARIC binding component that binds a target antigen contemplated herein, include but are not limited to, atezolizumab, avelumab, bavituximab, bevacizumab (avastin), bivatuzumab, blinatumomab, conatumumab, daratumumab, duligotumab, dacetuzumab, dalotuzumab, durvalumab, elotuzumab (Hu-Luc63), gemtuzumab, ibritumomab, indatuximab, inotuzumab, ipilimumab, lorvotuzumab, lucatumumab, milatuzumab, moxetumomab, nivolumab, ocaratuzumab, ofatumumab, pembrolizumab, rituximab, siltuximab, teprotumumab, and ublituximab.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones.

I. Therapeutic Methods

Immune effector cells modified to express a CD33 DARIC, a CD33 DARIC and an engineered antigen receptor, or a CD33 DARIC signaling component, a CD33 DARIC binding component and a DARIC binding component that binds another target antigen contemplated herein provide improved methods of adoptive immunotherapy for use in the prevention, treatment, and amelioration of, or for preventing, treating, or ameliorating at least one symptom associated with an immune disorder, e.g., cancer.

Immune effector cells comprising a DARIC signaling component, a CD33 DARIC binding component, and another DARIC binding component that binds CD7, CD13, CD15, CD30, CD38, CD44v6, CD45, CD47, CD70, CD123, CLL-1, FLT3, LeY, MICA, MICB, TIM3, ULBP1, ULBP2, ULBP3, ULBP4, ULBP5, ULBP6, VEGFR2, or WT-1 provide improved methods of adoptive immunotherapy for use in the prevention, treatment, and amelioration of, or for preventing, treating, or ameliorating at least one symptom associated with an immune disorder, e.g., cancer.

In particular embodiments, immune effector cells modified to express a CD33 DARIC signaling component and a CD33 DARIC binding component, and optionally a DARIC binding component that binds a target antigen provide improved methods of adoptive immunotherapy to fine-tune the safety and efficacy of a cytotoxic response against target cells, e.g., tumor cells, expressing target antigens while decreasing the risk of on-target antigen, off-target cell cytotoxicity (recognizing the target antigen on a normal, non-target cell).

In particular embodiments, a method of preventing, treating, or ameliorating at least one symptom of a cancer comprises administering the subject an effective amount of modified immune effector cells or T cells comprising one or more components of a CD33 DARIC signaling component and a CD33 DARIC binding component, and optionally a DARIC binding component that binds a target antigen and an engineered TCR, CAR, or other therapeutic transgene to redirect the cells to a target cell. The genetically modified cells are a more efficacious and safe cellular immunotherapy by virtue of transducing a chemically regulatable immunostimulatory signal.

In particular embodiments, one or more immune effector cells, e.g., T cells, are modified to express both a CD33 DARIC binding component and a CD33 DARIC signaling component, and optionally a DARIC binding component that binds a target antigen. In this case, the modified cells are administered to a subject in need thereof and home to the target cells via the interaction of the CD33 binding component expressed on the immune effector cell and CD33 expressed on the target cell and/or the interaction of the other DARIC binding component expressed on the immune effector cell and its target antigen expressed on the target cell. A bridging factor is administered to the subject before the modified cells, about the same time as the modified cells, or after the modified cells have been administered to the subject. In the presence of the bridging factor, a ternary complex forms between the CD33 DARIC binding component, the bridging factor, and the CD33 DARIC signaling component and if expressed, between the other DARIC binding component, the bridging factor, and the CD33 DARIC signaling component. Upon formation of the ternary complex, the DARIC(s) transduce an immunostimulatory signal to the immune effector cell that in turn, elicits a cytotoxic response from the immune effector cell against the target cell.

In particular embodiments, one or more immune effector cells, e.g., T cells, are modified to express a CD33 DARIC signaling component. In this case, the modified cells are administered to a subject in need thereof. A CD33 DARIC binding component, and optionally a DARIC binding component that binds a target antigen can be administered to the subject before the modified cells, about the same time as the modified cells, or after the modified cells have been administered to the subject. In addition, the CD33 DARIC binding component and/or the other DARIC binding component that binds a target antigen can be administered to the subject in a preformed complex with the bridging factor; at the same time as the bridging factor, but in a separate composition; or at a different time than the bridging factor. The CD33 binding component binds CD33 expressed on the target cell, and if present, the other DARIC binding component binds its target antigen expressed on the target cell, either in the presence or absence of the bridging factor. In the presence of the bridging factor, a ternary complex forms between the CD33 DARIC binding component, the bridging factor, and the CD33 DARIC signaling component and if present, between the other DARIC binding component, the bridging factor, and the CD33 DARIC signaling component. Upon formation of the ternary complex, the DARIC(s) transduce an immunostimulatory signal to the immune effector cell that in turn, elicits a cytotoxic response from the immune effector cell against the target cell.

In various embodiments, immune effector cells comprising a CD33 DARIC and/or an engineered antigen receptor fine-tune the safety and efficacy of a cytotoxic response against target cells using a dual targeting strategy wherein one or more target cells express one or more target antigens recognized by the engineered antigen receptor and CD33 recognized by the CD33 DARIC.

In particular embodiments, one or more immune effector cells, e.g., T cells, are modified to express both the CD33 DARIC binding component and the CD33 DARIC signaling component and an engineered antigen receptor, e.g., a CAR. In this case, the modified cells are administered to a subject in need thereof and home to the target cells via the interaction of the CD33 binding component and the CAR, both of which are expressed on the immune effector cell, and the target antigens expressed on the target cell. Interaction of the CAR with a target antigen on the target cell may elicit a cytotoxic response from the immune effector cell against the target cell. A bridging factor is administered to the subject before the modified cells, about the same time as the modified cells, or after the modified cells have been administered to the subject. In the presence of the bridging factor, a ternary complex forms between the CD33 DARIC binding component, the bridging factor, and the CD33 DARIC signaling component. Upon formation of the ternary complex, the CD33 DARIC transduces an immunostimulatory signal to the immune effector cell that in turn, elicits or augments a cytotoxic response from the immune effector cell against the target cell. In particular embodiments, CD33 DARIC receptor activation can be induced in cases where remission or regression is incomplete and the condition relapses or becomes refractory to treatment.

In particular embodiments, one or more immune effector cells, e.g., T cells, are modified to express the CD33 DARIC signaling component. In this case, the modified cells are administered to a subject in need thereof. A CD33 DARIC binding component can be administered to the subject before the modified cells, about the same time as the modified cells, or after the modified cells have been administered to the subject. In addition, the CD33 DARIC binding component can be administered to the subject in a preformed complex with the bridging factor; at the same time as the bridging factor, but in a separate composition; or at a different time than the bridging factor. The CD33 binding component binds the target antigen expressed on the target cell, either in the presence or absence of the bridging factor. In the presence of the bridging factor, a ternary complex forms between the CD33 DARIC binding component, the bridging factor, and the CD33 DARIC signaling component. Upon formation of the ternary complex, the CD33 DARIC transduces an immunostimulatory signal to the immune effector cell that in turn, elicits a cytotoxic response from the immune effector cell against the target cell. In particular embodiments, CD33 DARIC activation can be induced in cases where remission or regression is incomplete and the condition relapses or becomes refractory to treatment.

In particular preferred embodiments, the specificity of a primary T cell is redirected to tumor or cancer cells that express CD33 by genetically modifying a T cell, e.g., a primary T cell, with one or more CD33 DARIC components.

In particular preferred embodiments, the specificity of a primary T cell is redirected to tumor or cancer cells that express CD33 by genetically modifying a T cell, e.g., a primary T cell, with an engineered antigen receptor directed to the target antigen and one or more CD33 DARIC components.

In particular preferred embodiments, the specificity of a primary T cell is redirected to tumor or cancer cells that express (i) CD33 and (ii) another target antigen, by genetically modifying a T cell, e.g., a primary T cell, with one or more CD33 DARIC components and one or more other DARIC binding components that bind the target antigen.

In particular preferred embodiments, the specificity of a primary T cell is redirected to tumor or cancer cells that express (i) CD33 (a first target antigen) and (ii) another target antigen (a second target antigen), by genetically modifying a T cell, e.g., a primary T cell, with an engineered antigen receptor directed to a third target antigen and one or more CD33 DARIC components and one or more other DARIC binding components that bind the second target antigen.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, non-small cell lung carcinoma, head and neck squamous cell carcinoma, colorectal cancer, pancreatic cancer, breast cancer, thyroid cancer, bladder cancer, cervical cancer, esophageal cancer, ovarian cancer, gastric cancer endometrial cancer, gliomas, glioblastomas, and oligodendroglioma.

In particular embodiments, the modified immune effector cells contemplated herein are used in the treatment of solid tumors or cancers including, without limitation, non-small-cell lung cancer, metastatic colorectal cancer, glioblastoma, head and neck cancer, pancreatic cancer, and breast cancer.

In particular embodiments, the modified immune effector cells contemplated herein are used in the treatment of glioblastoma.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In particular embodiments, the modified immune effector cells contemplated herein are used in the treatment of acute myeloid leukemia (AML).

Preferred cells for use in the methods contemplated herein include autologous/autogeneic ("self") cells, preferably hematopoietic cells, more preferably T cells, and more preferably immune effector cells.

In particular embodiments, a method comprises administering a therapeutically effective amount of modified immune effector cells that express one or more CD33 DARIC components, and optionally an engineered antigen receptor or another DARIC binding component, or a composition comprising the same, to a patient in need thereof, and also administering a bridging factor to the subject. In certain embodiments, the cells are used in the treatment of patients at risk for developing an immune disorder. Thus, particular embodiments comprise the treatment or prevention or amelioration of at least one symptom of an immune disorder, e.g., cancer, comprising administering to a subject in need thereof, a therapeutically effective amount of the modified immune effector cells contemplated herein and a bridging factor.

In particular embodiments, a method comprises administering a therapeutically effective amount of modified immune effector cells that express a CD33 DARIC signaling component, and optionally an engineered antigen receptor or another DARIC binding component, or a composition comprising the same, to a patient in need thereof, and also administering a CD33 DARIC binding component and a bridging factor, optionally wherein the CD33 DARIC binding component is bound to the bridging factor prior to administration, to the subject. In certain embodiments, the cells are used in the treatment of patients at risk for developing an immune disorder. Thus, particular embodiments comprise the treatment or prevention or amelioration of at least one symptom of an immune disorder, e.g., cancer, comprising administering to a subject in need thereof, a therapeutically effective amount of the modified immune effector cells that express a CD33 DARIC signaling component and optionally and engineered antigen receptor or another DARIC binding component, a CD33 DARIC binding component, and a bridging factor.

The quantity and frequency of administration of modified immune effector cells, CD33 DARIC binding components, and/or bridging factor will be determined by such factors as the condition of the patient, and the type and severity of the patient's disease, although appropriate dosages and dose schedules may be determined by clinical trials.

In one illustrative embodiment, the effective amount of modified immune effector cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of modified immune effector cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of modified immune effector cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more. Modified immune effector cells, CD33 DARIC components, and bridging factor may be administered in the same or different compositions; in one or more compositions at the same time; or more than one composition at different times. Modified immune effector cells, CD33 DARIC components, and bridging factor may be administered through the same route of administration or different routes.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding one or more CD33 DARIC components into the cell and producing a population of modified immune effector cells, and administering the population of modified immune effector cells to the same subject. In a preferred embodiment, the immune effector cells comprise T cells.

In one embodiment, a method of treating a subject diagnosed with a cancer, comprises removing immune effector cells from the subject, modifying the immune effector cells by introducing one or more vectors encoding one or more CD33 DARIC components and optionally an engineered antigen receptor or another DARIC binding component into the cell and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or reintroduction of modified progenitors of immune effector cells that upon introduction into a subject differentiate into mature immune effector cells. One method comprises modifying peripheral blood T cells ex vivo by introducing one or more vectors encoding one or more CD33 DARIC components and optionally an engineered antigen receptor or another DARIC binding component into the cell and returning the transduced cells into the subject.

The methods for administering the cell compositions contemplated in particular embodiments include any method which is effective to result in reintroduction of ex vivo modified immune effector cells or reintroduction of modified progenitors of immune effector cells that upon introduction into a subject differentiate into mature immune effector cells. One method comprises modifying peripheral blood T cells ex vivo by introducing one or more vectors encoding one or more CD33 DARIC components and optionally an engineered antigen receptor or another DARIC binding component into the cell and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by

EXAMPLES

Example 1

Drug-Regulatable CD33 Daric T Cell Response Against Tumor Cells

CD33 DARIC lentiviral plasmids containing an MNDU3 promoter operably linked to a polynucleotide encoding a CD8α-derived signal peptide, a FRB domain variant (T82L), a CD8α derived transmembrane domain, a 4-1BB costimulatory domain, and a CD3ζ signaling domain, a P2A sequence, a Ig-derived signal peptide, one of two anti-CD33 scFvs (SEQ ID NOs: 2-3), a FKBP12 domain and a CD4 derived transmembrane and truncated intracellular domain (SEQ ID NO: 4-5) were designed, constructed, and verified. FIG. 1.

Human PBMCs ($1\times10^6$ cells/mL) were activated with soluble anti-CD3 and anti-CD28 antibodies (50 ng/ml) on day 0. After 24 hr incubation, $1\times10^6$ cells were transduced with a lentivirus encoding CD33 DARIC-1 or CD33 DARIC-2. The cells were washed and resuspended at $0.3\times10^6$ cells/mL on day 3. The cells were cultured for 7 days with IL-2 (250 IU/mL) containing medium changed every other day. CD33 DARIC binding component expression on transduced T cells was analyzed by staining with recombinant CD33-Fc or antibodies to anti-CD33 scFv.

On day 10, transduced T cells and untransduced control T cells were co-cultured with CD33$^+$ THP-1 or CD33$^+$ Molm-1 tumor cell lines for 48 hr at a 1:1 effector:target ratio (E:T). CD33 DARIC-1 T cells and CD33 DARIC-2 T cells demonstrate cytotoxic responses against CD33$^+$ THP-1 or CD33$^+$ Molm-1 tumor cell lines in the presence of rapamycin or the non-immunosuppressive rapalog AP21967.

Cytokine production of CD33 DARIC-1 T cells and CD33 DARIC-2 T cells was measured after 24 hours of co-culture with CD33$^+$ THP-1 or CD33$^+$ Molm-1 tumor cell lines at a 1:1 E:T ratio in the presence or absence of rapamycin or AP21967. Culture supernatants were collected and cytokine production (IFNγ, IL-2, TNFα, IL-17α, IL-4 and IL-6) was analyzed using the Qbead PlexScreen cytokine assay kit (Intellicyt). CD33 DARIC-1 T cells and CD33 DARIC-2 T cells will produce cytokines only in the presence of rapamycin or AP21967.

Example 2

CD33 DARIC Binding Components Containing a Costimulatory Domain

Figure 2A:
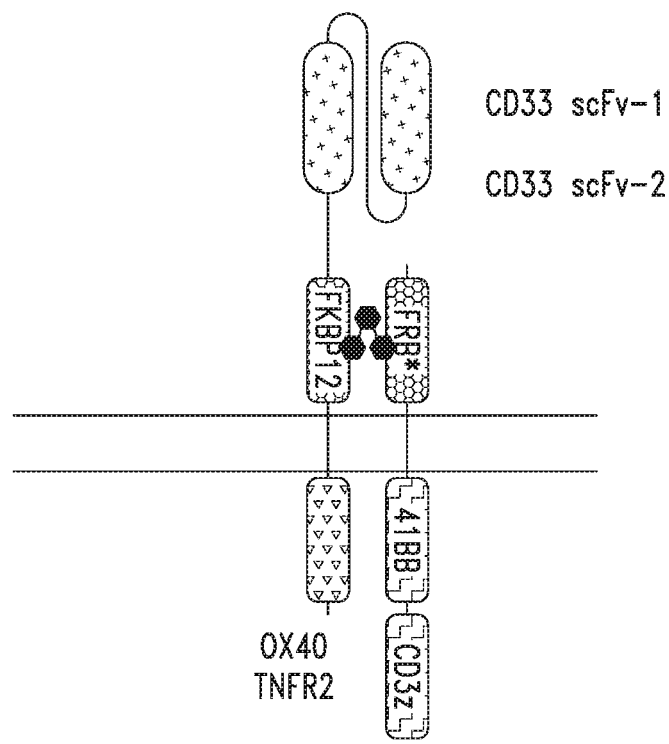
FIG. 2A shows a cartoon of anti-CD33 DARIC architecture with costimulatory domains.

CD33 DARIC binding and signaling components were designed, constructed, and verified. CD33 DARIC lentiviral vectors were constructed comprising an MNDU3 promoter operably linked to a polynucleotide encoding: a DARIC signaling component (CD8α-signal peptide, an FRB variant (T82L), a CD8α transmembrane domain, an intracellular 4-1BB costimulatory domain, and a CD3 (signaling domain); a P2A sequence; and a DARIC binding component (an Igκ-signal peptide, one of two an anti-CD3 scFv binding domains, a G4S linker, an FKBP12 domain, a CD4 transmembrane domain and an OX40 costimulatory domain or TNFR2 costimulatory domain). FIG. 2A; SEQ ID NOs: 6-9.

Figure 2B:
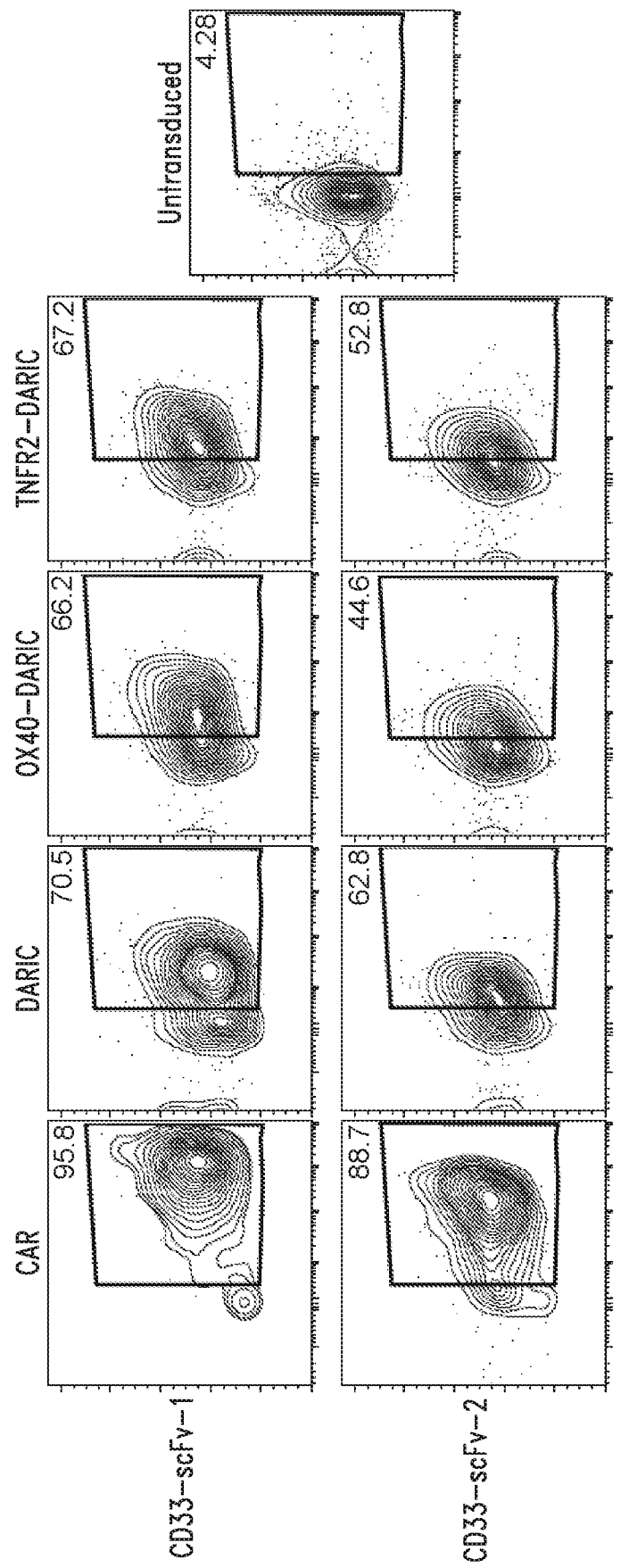
FIG. 2B shows CD33-Fc binding efficiency for untransduced T cells, anti-CD33 CAR T cells, anti-CD33 DARIC T cells, CD33.OX40 DARIC T cells and CD33.TNFR2 DARIC T cells. Two different anti-CD33 scFvs are shown.

Human PBMCs were activated, transduced and expanded as described in Example 1. UTD T cells, anti-CD33 (scFv-1) CAR T cells, anti-CD33 (scFv-2) CAR T cells, CD33 (scFv-1) DARIC T cells, CD33 (scFv-2) DARIC T cells, CD33.OX40 (scFv-1) DARIC T cells, CD33.OX40 (scFv-2) DARIC T cells, CD33.TNFR2 (scFv-1) DARIC T cells, and CD33.TNFR2 (scFv-2) DARIC T cells displayed similar rates of ex vivo expansion. The T cells were stained with recombinant CD33-Fc protein and anti-CD33 scFv expression was quantified on CD4$^+$ T cells. Expression was comparable among the different CD33 DARIC binding components. FIG. 2B.

Figure 2C:
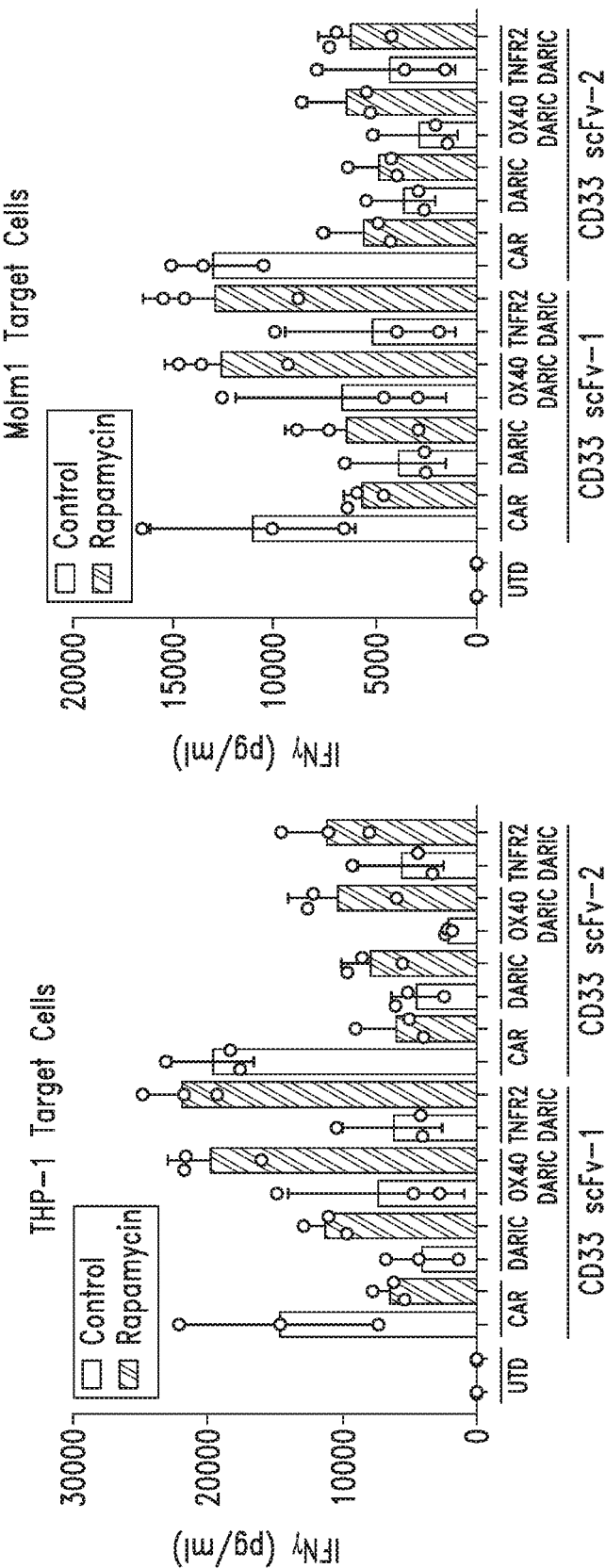
FIG. 2C shows IFNγ production from culture supernatants of CD33⁺ THP-1 or CD33₊ Molm-1 cells co-cultured for 24 hrs with ant-CD33 CAR T cells, CD33 DARIC T cells, CD33.OX40 DARIC T cells, and CD33.TNFR2 DARIC T cells at a 1:1 E:T ratio in Vehicle or Rapamycin. Two different anti-CD33 scFvs are shown.
Figure 3:
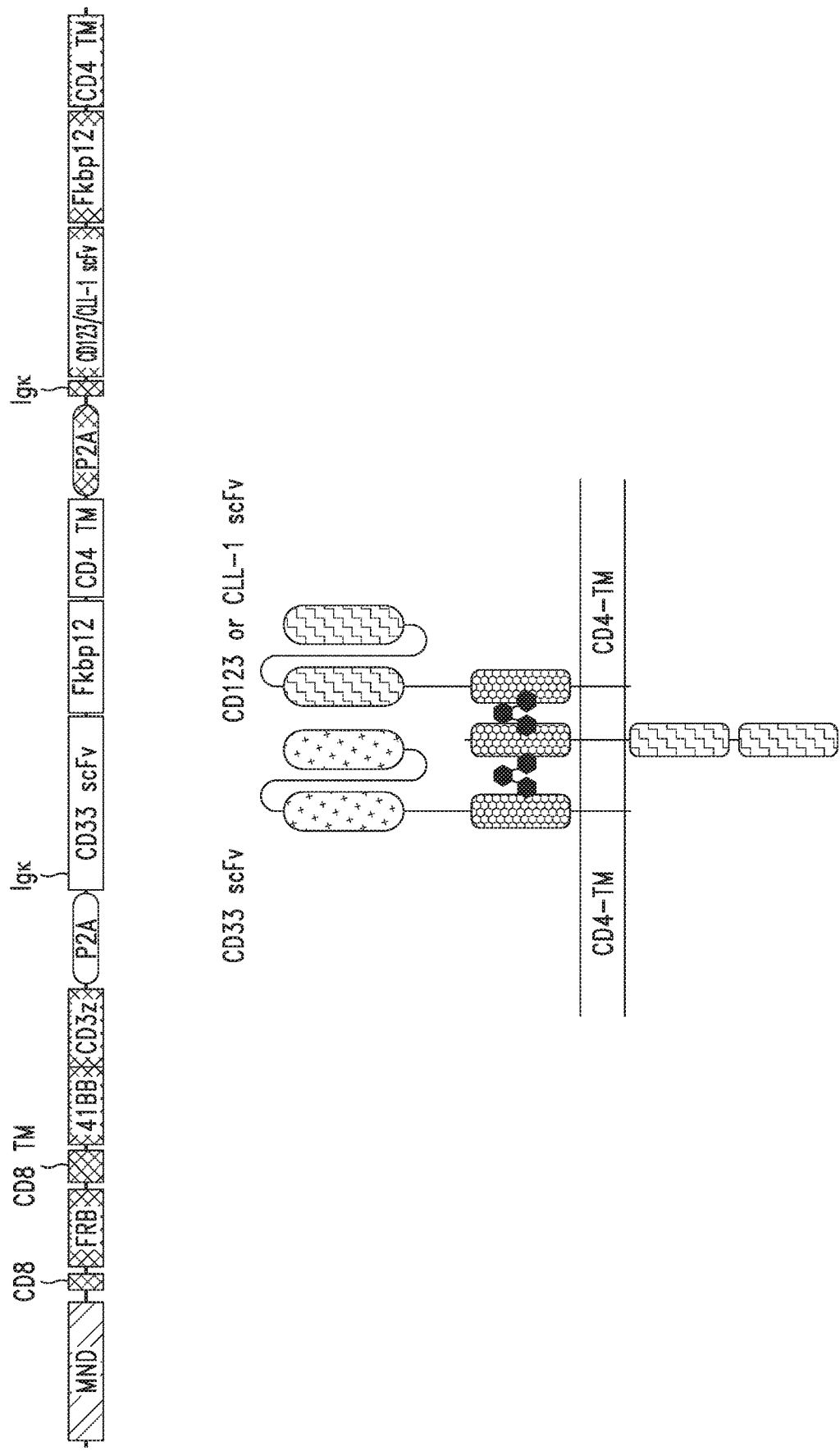
FIG. 3 shows a cartoon of a dual targeting EGFRvIII DARIC/HER2 DARIC fusion protein.

UTD T cells, anti-CD33 (scFv-1) CAR T cells, anti-CD33 (scFv-2) CAR T cells, CD33 (scFv-1) DARIC T cells, CD33 (scFv-2) DARIC T cells, CD33.OX40 (scFv-1) DARIC T cells, CD33.OX40 (scFv-2) DARIC T cells, CD33.TNFR2 (scFv-1) DARIC T cells, and CD33.TNFR2 (scFv-2) DARIC T cells were co-incubated with CD33$^+$ THP-1 or CD33$^+$ Molm-1 tumor cell lines at 1:1 E:T ratio for 24 hrs. with or without rapamycin. Cytokine production was measured from culture supernatants using a Qbead assay kit. CD33 DARICs comprising binding components with a costimulatory domain showed consistent increases in cytokine production in the presence of rapamycin compared to anti-CD33 CAR T cells and CD33 DARIC T cells. FIG. 2C.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

The invention claimed is:

1. A non-natural cell comprising:
   (a) a first polypeptide comprising i) an FKBP-rapamycin binding (FRB) multimerization domain polypeptide; ii) a cluster of differentiation (CD)8α transmembrane domain; iii) a CD137 co-stimulatory domain; and iv) a CD3 ζ primary signaling domain; and
   (b) a second polypeptide comprising i) a binding domain that binds to CD33, wherein the binding domain that binds to CD33 is a single chain Fv protein (scFv) comprising the amino acid sequence of SEQ ID NO:2; ii) an FK506 binding protein (FKBP) multimerization domain polypeptide; and iii) a CD4 transmembrane domain;
   wherein the FKBP multimerization domain polypeptide is FKBP12 and wherein the FRB multimerization domain polypeptide is FRB T2098L.

2. The non-natural cell of claim 1, wherein a bridging factor promotes formation of a polypeptide complex on the non-natural cell surface, wherein the bridging factor associates with the first and second polypeptides between the multimerization domains of the first and second polypeptides, and wherein the bridging factor is selected from the group consisting of AP21967, sirolimus, everolimus, novolimus, pimecrolimus, ridaforolimus, tacrolimus, temsirolimus, umirolimus, and zotarolimus.

3. The non-natural cell of claim 1, wherein the second polypeptide comprises a costimulatory domain.

4. The non-natural cell of claim 3, wherein the costimulatory domain of the second polypeptide is selected from a costimulatory molecule selected from the group consisting of Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNA polymerase III subunit gamma/tau (DNAX)-activation protein 10 (DAP10),
linker for activation of T-cells family member 1 (LAT), Src Homology 2 (SH2) domain-containing leukocyte protein of 76 kD (SLP76), T cell receptor associated transmembrane adaptor 1 (TRAT1), tumor necrosis factor receptor superfamily member 14 (TNFRS14), TNFRS18, TNRFS25, and zeta chain of T cell receptor associated protein kinase 70 (ZAP70).

5. The non-natural cell of claim 4, wherein the costimulatory domain of the second polypeptide is OX40.

6. The non-natural cell of claim 1, wherein the first polypeptide, the second polypeptide, or both comprise a signal peptide.

7. The non-natural cell of claim 1, wherein the first polypeptide comprises a CD8α signal peptide.

8. The non-natural cell of claim 1, wherein the second polypeptide comprises an Igκ signal peptide.

9. A composition comprising the non-natural cell of claim 1.

10. A pharmaceutical composition comprising a pharmaceutically acceptable carrier and the non-natural cell of claim 1.

* * * * *